United States Patent
Anand et al.

(10) Patent No.: US 10,537,860 B2
(45) Date of Patent: Jan. 21, 2020

(54) EMULSIONS BY CONDENSATION

(71) Applicant: Massachusetts Institute of Technology, Cambridge, MA (US)

(72) Inventors: Sushant Anand, Somerville, MA (US); Seyed Reza Mahmoudi, Waltham, MA (US); Ingrid Fuller Guha, Cambridge, MA (US); Kripa Kiran Varanasi, Lexington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/318,349

(22) PCT Filed: Jun. 23, 2015

(86) PCT No.: PCT/US2015/037273
§ 371 (c)(1),
(2) Date: Dec. 12, 2016

(87) PCT Pub. No.: WO2015/200381
PCT Pub. Date: Dec. 30, 2015

(65) Prior Publication Data
US 2017/0197187 A1    Jul. 13, 2017

Related U.S. Application Data

(60) Provisional application No. 62/015,634, filed on Jun. 23, 2014.

(51) Int. Cl.
*B01F 3/08* (2006.01)
*A61K 9/107* (2006.01)
*B01F 17/00* (2006.01)

(52) U.S. Cl.
CPC .......... *B01F 3/0811* (2013.01); *A61K 9/107* (2013.01); *B01F 17/00* (2013.01); *A61K 9/1075* (2013.01);
(Continued)

(58) Field of Classification Search
CPC ....... A61K 9/107; B01F 3/0811; B01F 17/00; B01F 2003/0842; B01F 2003/0846; B01F 2003/0823; B01F 2003/0838
See application file for complete search history.

(56) References Cited

U.S. PATENT DOCUMENTS

| 7,485,671 B2 | 2/2009 | Qiu et al. |
| 2007/0191314 A1 | 8/2007 | Klucker et al. |

(Continued)

FOREIGN PATENT DOCUMENTS

| RU | 2349631 C1 | 3/2009 |
| WO | 2014/055539 A1 | 4/2014 |

OTHER PUBLICATIONS

Sumner, J. Phys. Chem. 37, 279-302 (1933).*
(Continued)

*Primary Examiner* — Theodore R. West
(74) *Attorney, Agent, or Firm* — Steptoe & Johnson LLP

(57) ABSTRACT

Nanoscale emulsions can be made by means of condensing a liquid vapor onto another liquid. The precise size, chemical composition, and density of emulsions may be controlled through varying the experimental parameters, such as surfactant concentration, time of condensation, humidity, and temperature.

29 Claims, 20 Drawing Sheets

(52) U.S. Cl.
CPC ............. *B01F 2003/0823* (2013.01); *B01F 2003/0838* (2013.01); *B01F 2003/0842* (2013.01)

(56) References Cited

U.S. PATENT DOCUMENTS

| | | |
|---|---|---|
| 2008/0182910 A1 | 7/2008 | Qiu et al. |
| 2011/0165206 A1 | 7/2011 | Liu et al. |
| 2012/0315308 A1 | 12/2012 | Travers |
| 2013/0149261 A1 | 6/2013 | DelValle et al. |
| 2013/0197100 A1 | 8/2013 | Cerize et al. |

OTHER PUBLICATIONS

Notification Concerning Transmittal of International Preliminary Report on Patentability (Chapter I of the Patent Cooperation Treaty) dated Jan. 5, 2017, issued in International Application No. PCT/US2015/037273.

International Search Report dated Sep. 15, 2015, issued in International Application No. PCT/US2015/037273.

Written Opinion of the International Searching Authority dated Sep. 15, 2015, issued in International Application No. PCT/US2015/037273.

\* cited by examiner

EMULSIONS BY CONDENSATION

CLAIM OF PRIORITY

This application claims the benefit under 35 USC 371 to International Application No. PCT/US2015/037273, filed Jun. 23, 2015, which claims the benefit of prior U.S. Provisional Application No. 62/015,634, filed Jun. 23, 2014, each of which is incorporated by reference in its entirety.

STATEMENT REGARDING FEDERALLY SPONSORED RESEARCH OR DEVELOPMENT

This invention was made with Government support under Grant No. CBET-0952564 awarded by the National Science Foundation. The Government has certain rights in the invention.

TECHNICAL FIELD

This invention relates to a method of making emulsions.

BACKGROUND

In general, emulsions can be formed by dispersing liquid droplets (dispersed phase) in another immiscible or partly miscible liquid (continuous phase). Two liquids can form different types of emulsions. For example, oil and water can form, an oil-in-water emulsion, wherein the oil is the dispersed phase, and water is the continuous phase. Alternatively, they can form a water-in-oil emulsion, wherein water is the dispersed phase and oil is the continuous phase. Multiple emulsions are also possible, including a "water-in-oil-in-water" emulsion and an "oil-in-water-in-oil" emulsion.

Emulsions can be formed either by mechanical disintegration of bulk liquid into the fine droplets forming the disperse phase, or by phase-inversion technique (where the dispersed phases and continuous phases of the system are exchanged i.e. oil in water emulsion, may be reverted to a water in oil and vice versa). Other techniques rely on using flow devices where the dispersed phase is injected into the continuous phase through membranes or through nozzles/microchannels embedded in substrates.

SUMMARY

A method of making an emulsion can include vaporizing a primary liquid, selecting a secondary liquid and an emulsifier to permit formation of an emulsion, wherein the primary liquid and the secondary liquid are immiscible or partly miscible, and forming a mixture of the primary liquid, the secondary liquid and the emulsifier under thermodynamic conditions that are below the dew point of the primary liquid. The emulsifier concentration can be larger than a minimum critical concentration. This can cause vapor to liquid phase change of the primary liquid, and where the emulsifier adsorbs at the interface of the primary liquid and the secondary liquid. The size of dispersed phase may range from nanoscale to microscales (1 nm-1000 μm). In certain embodiments, the emulsion size can be monomodal with narrow polydispersity in microscales (polydispersity of droplet sizes<20%). In certain embodiments, the emulsion size can be monomodal with narrow polydispersity in nanoscale (polydispersity of droplet sizes<20%). In certain embodiments, the nanoscale monodisperse emulsion can be directly formed without further processing to reduce emulsion size.

The primary liquid can be a pure chemical compound or mixture of several chemical compounds operated under thermodynamic conditions where each chemical compound exists in the vapor state.

The emulsifier can be a surfactant or nanoparticles or combination of multiple surfactants/nanoparticles.

The secondary liquid can be a pure chemical compound or homogeneous mixture of several chemical compounds in liquid state. In case where the secondary liquid and the primary liquid (or some component within the primary liquid) are partly miscible, the primary liquid (or the partly miscible component) may dissolve until the miscibility limit is attained and the dispersed phase of the primary liquid (in form of droplets) may thereafter be formed.

A temperature of the secondary liquid can be below the dew point of the primary liquid. In case the primary liquid is a mixture of several compounds, the temperature of the secondary liquid can be below the dew point of the lowest dew point compound of the primary liquid. In certain embodiments, the primary liquid can be water and the secondary liquid can be oil. In certain other embodiments, the primary liquid can be oil and the secondary liquid can be water. In certain other embodiments, the primary liquid can be a first oil and the secondary liquid can be a second oil. In certain other embodiments, the primary liquid can be a combination of several oils or oil-water and the secondary liquid can be a combination of several oils of chemical nature other than the first oil.

The method of making an emulsion can further comprise superheating the vaporized liquid before condensing. Vaporization of the primary liquid can be achieved by several methods including but not limited to: evaporating the primary liquid by heating, boiling the primary liquid, aerosolizing and then heating the aerosol droplets of primary liquid, or decreasing the pressure surrounding the primary liquid.

In certain embodiments, the method of making an emulsion can further comprise flowing the secondary liquid and the vaporized primary liquid while condensing the vaporized primary liquid. In certain other embodiments, the method of making an emulsion can further comprise agitating the secondary liquid while condensing the vaporized primary liquid. In certain other embodiments, condensing the primary liquid on the secondary liquid can include injecting the vaporized primary liquid into the secondary liquid. In certain other embodiments, condensing the primary liquid on the secondary liquid can include using jet impingement of the vaporized liquid. In certain other embodiments, condensing the primary liquid on the secondary liquid can include injecting through channels (micron/millimeter size) or membranes or porous walls within the secondary liquid-emulsifier mixture.

The method of making an emulsion can further include vaporizing the emulsions and condensing the emulsion on a tertiary liquid.

A method of making an emulsion can include vaporizing a primary liquid, selecting a secondary liquid, a tertiary liquid and an emulsifier to permit formation of an emulsion, wherein the primary liquid and the secondary liquid are immiscible or partly miscible, and condensing the primary liquid on a mixture of the secondary liquid and the tertiary liquid, wherein the secondary liquid is miscible with the tertiary liquid and the tertiary liquid is immiscible or partly miscible with the primary liquid. In certain embodiments, the primary liquid can be water, the secondary liquid can be a first oil, and the tertiary liquid can be a second oil. In certain embodiments, the primary liquid can be water, the secondary liquid can be a combination of oils, and the tertiary liquid can be combination of oils of chemical nature other than the components of second oil.

Other aspects, embodiments, and features will be apparent from the following description, the drawings, and the claims.

BRIEF DESCRIPTION OF THE DRAWINGS

FIG. 2A is a representative image showing no observable condensation after two hours within the liquid when the liquid temperature is greater than dew point ($T_{dew-point}$) but less than room temperature ($T_{room-temp}$). FIG. 2B is a representative image showing condensation at liquid-air interface when temperature is reduced below the dew point. Scale bars represent 20 µm. The liquid here is a silicone oil of viscosity 10 cSt, and the vapor being condensed is water vapor.

FIG. 4A shows injection of vapor in a subcooled oil via a nozzle/tube immersed within the subcooled liquid. FIG. 4B shows vapor impinging on the subcooled oil.

FIG. 6A shows injection of vapors of two liquids in a subcooled oil. FIG. 6B shows two vapors injected into the subcooled oil, where the two vapors may interact with each other prior to interacting with the subcooled oil. By regulating the temperature of vapors, it is possible to form a droplet of one vapor encapsulating the droplet of the other vapor. The encapsulated droplet can then interact with the oil-emulsifier mixture and form emulsion.

FIG. 7C shows the formation of nanoemulsions during vapor condensation on oil-surfactant mixture.

DETAILED DESCRIPTION

Figure 1:
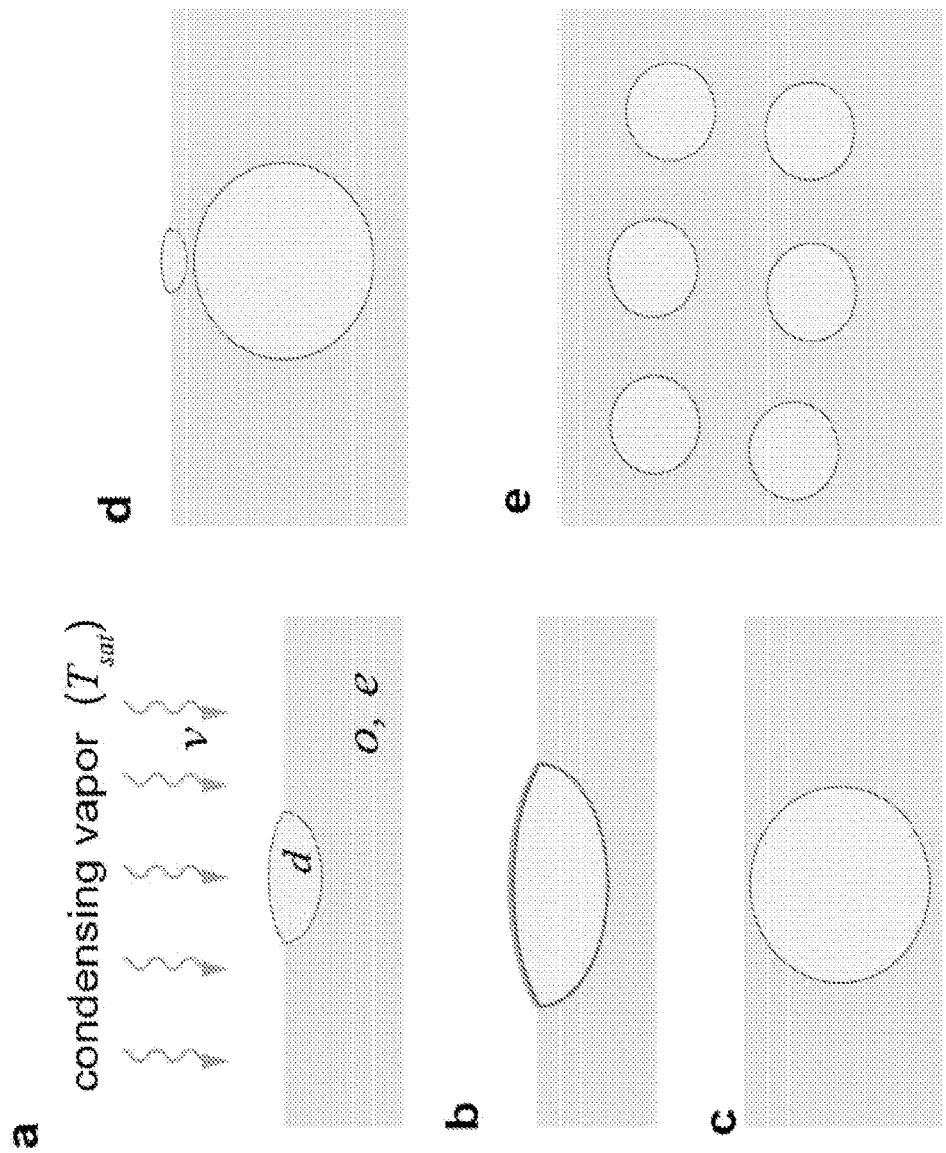
FIG. 1 shows a schematic of an embodiment and idea behind the disclosed method.

Emulsions are a class of products where liquid droplets (a primary liquid in dispersed phase and referred henceforth as droplet, subset 'd') are dispersed in another immiscible or partly miscible liquid (a secondary liquid that provides a continuous phase and referred henceforth as oil, subset 'o') in presence of a third agent that adsorbs at the droplet-oil interface. In case where the oil and the droplets are partly miscible, the droplets may dissolve until the miscibility limit is attained and the droplets may be formed thereafter. See, Tharwat F Tadros, *Emulsion science and technology: a general introduction*. Emulsion science and technology. Wiley-VCH, Weinheim, 2009: p. 1-56, which is incorporated by reference in its entirety. The third agent is added to the system to stabilize the emulsion for long-term usage (referred henceforth as emulsifier, subset 'e'). The third agent maybe a liquid itself (e.g. a surfactant or a combination of different surfactants) or nanoparticles, or a combination of both, or the third agent may be a solid that may be partially miscible with the continuous phase. The term "surfactant" is of common usage and generally refers to compounds that decrease interfacial tension of a liquid/liquid interface or an air/liquid interface upon adsorption at their interface. The primary requirement for the third agent is that such agents adsorb at the liquid/liquid (i.e. droplet-oil) interface forming a protective shell around emulsion droplets and thereby delaying coalescence with neighboring droplets with similar attributes. In certain circumstances, where the third agent is a surfactant, a minimum concentration of surfactant in the continuous phase is required to form stable emulsions where the stability is defined as any prevention or delay of immediate coalescence between droplets (the dispersed phase) upon contact. The minimum concentration of surfactant required to make a stable emulsion generally corresponds to its critical micelle concentration (CMC). At concentrations higher than the CMC, the surfactant may form precipitates known as micelles within the oil. The interfacial tension between the droplet and the oil declines significantly with increasing surfactant concentration until the CMC value is reached. Above CMC, the interfacial tension decreases only very slightly with increasing surfactant concentration. In certain circumstances, where the third agent is a nanoparticle, a minimum concentration of nanoparticle concentration within the continuous phase corresponds to the equilibrium concentration at which the nanoparticles have maximum adsorption at the droplet-oil interface.

Disclosed herein is a method and a system to manufacture emulsions by means of condensing vapor of the primary liquid on the secondary liquid in presence of a minimum concentration of an emulsifier; specifically, by formation of droplets of the primary liquid on or within the secondary liquid through nucleation, wherein droplet nucleation occurs via contact of the vapor phase of the primary liquid with secondary liquid-emulsifier mixture in thermodynamic conditions wherein nucleation of the primary liquid is favorable. The emulsifier can include a surfactant or nanoparticles or combination of multiple surfactants/nanoparticles.

The key feature is the ease with which such emulsions can be made; the state-of-the-art, on the other hand, relies on using mechanical means like stirring, or thermodynamic techniques like phase inversion. The disclosed method is fundamental in nature and hence can be potentially used in all applications where emulsions are used; some examples are—making phase change materials for heat transfer, cosmetics, food emulsions, agrochemicals, pharmaceuticals, paints, automobile oils, fuels, etc. See Laurier L Schramm, *Emulsions, foams, and suspensions: fundamentals and applications.* 2006: John Wiley & Sons, which is incorporated by reference in its entirety.

Typical methods for producing emulsions involve the following techniques.

Shear based emulsification utilizes agitation of liquid/oil system in a pipe, static mixers and general mixers, high-speed mixers, colloid-mills and high-pressure homogenizers, ultrasonic agitation etc. See, Tharwat F Tadros, *Emulsion science and technology: a general introduction.* Emulsion science and technology. Wiley-VCH, Weinheim, 2009: p. 1-56, which is incorporated by reference in its entirety. The flow may be either laminar or turbulence, and the oil viscosity plays an important part in break-up of droplets. The droplets produced through this method are highly polydisperse in size. Conventional emulsification devices, such as rotor-stator systems and high-pressure homogenizers, were first used to produce emulsions and to use extensional and shear stress or impact to rupture the droplets. For producing very small droplet sizes the turbulent flow is generally required.

In phase inversion technique, the dispersed phases and continuous phases of the system are exchanged with each other. For example, an agitated oil in water emulsion may be reverted to a water in oil and vice versa. See, P. Izquierdo, J. Esquena, Th F. Tadros, C. Dederen, M. J. Garcia, N. Azemar, and C. Solans, *Formation and stability of nano-emulsions prepared using the phase inversion temperature method.* Langmuir, 2002. 18(1): p. 26-30, P. Fernandez, V. André, J. Rieger, and A. Kühnle, *Nano-emulsion formation by emulsion phase inversion.* Colloids and Surfaces A: Physicochemical and Engineering Aspects, 2004. 251(1-3): p. 53-58, W. Liu, D. Sun, C. Li, Q. Liu, and J. Xu, *Formation and stability of paraffin oil-in-water nano-emulsions prepared by the emulsion inversion point method.* Journal of Colloid and Interface Science, 2006. 303(2): p. 557-563, each of which is incorporated by reference in its entirety.

Emulsions can be made using Ouzo Effect. See, S. A. Vitale and J. L. Katz, *Liquid droplet dispersions formed by homogeneous liquid-liquid nucleation: "The ouzo effect".* Langmuir, 2003. 19(10): p. 4105-4110, which is incorporated by reference in its entirety. In this method, oil droplet dispersions are formed in water by adding water to a solution of oil and solvent, where the oil and solvent are miscible with each other. This leads to supersaturation of oil to supersaturate, and nucleation into smaller droplets.

Membranes can be used for producing emulsions. See, Tharwat F Tadros, *Emulsion science and technology: a general introduction.* Emulsion science and technology. Wiley-VCH, Weinheim, 2009: p. 1-56, which is incorporated by reference in its entirety. Here the droplet phase is injected through membranes directly into the continuous phase, or a pre-mixed polydisperse phase of droplet-oil solution is injected into membrane to produce monomodal droplets with narrow polydispersity in oils.

Microchannel array devices can produce emulsions. Here the droplet phase is generated by pumping a dispersed phase through a narrow microchannel and directly injected in an oil. See, Tharwat F Tadros, *Emulsion science and technology: a general introduction.* Emulsion science and technology. Wiley-VCH, Weinheim, 2009: p. 1-56, which is incorporated by reference in its entirety.

Vapor condensation on oils leading to formation of dispersed phases in a continuous medium may occur in few situations. In petrochemical industry, a method for recovering oil from the underground rocks or sands involves direct injection of steam in such systems. See, Peter Vanmeurs, Harold J Vinegar, and Monroe H Waxman, In-situ steam drive oil recovery process, 1987, Google Patents, and A J Cornelius. *Laboratory studies of oil recovery by steam injection.* in *Paper presented at 35th Annual Fall Meeting-of SPE.* October 1961, each of which is incorporated by reference in its entirety. The injected steam eventually condenses into water upon contact with the oil or the solid surface and may form a mixed state of water-droplets and oil. See, J Bruining and D Marchesin, *Maximal oil recovery by simultaneous condensation of alkane and steam.* Physical Review E, 2007. 75(3): p. 036312, and A. R. Kovscek, *Emerging challenges and potential futures for thermally enhanced oil recovery.* Journal of Petroleum Science and Engineering, 2012. 98-99: p. 130-143, each of which is incorporated by reference in its entirety. However, the formation of such state is accidental, and not practiced as a deliberate process for manufacturing emulsions. Further, the emulsion like state so produced is later subjected to different chemical techniques to extract the oil, and the emulsified oil is itself not used as a product. On the other hand, here the idea is based on using the method of vapor condensation on immiscible or partly miscible liquids in presence of an emulsifier for the explicit purpose of creating emulsions that can be used widely for different applications.

In another instance, droplet formation on a secondary liquid in presence of an emulsifier was obtained through injection of the vapor phase of the primary liquid within the secondary liquid-emulsifier mixture. See, for example, Sumner, C. G., *On the formation, size, and stability of emulsion particles I: a new method of emulsification*, J. Phys. Chem., 1933, 37 (3), pp 279-302, which is incorporated by reference in its entirety. Sumner generated an oil-in-water emulsion by injection of benzene vapor through a nozzle within a water bath with dissolved amphiphilic salt (an anionic salt called sodium oleate). Droplets of size ~ order of 10 μm were measured, however the precise measurements were impossible due to lack of experimental techniques to accurately determine the droplet sizes. Although in the Sumner work, the method of vapor injection is used, the origin of droplet formation was unclear. Firstly, the injection of the vapor was performed at temperatures closer or larger than the boiling temperature of the secondary liquid (water) that also lead to vaporization of the secondary liquid. It was speculated that the droplets had either formed in vapor phase itself and then got submerged due to the high exit pressure of the nozzle; or they could have been formed within the oil. Secondly, it is not clear if the amphiphilic salt concentration was larger than its CMC (critical micelle concentration) in water. The CMC of sodium oleate at 25° C. is ~2.15-3.0 mM, whereas the concentrations used by the author (2.5 mM and below) are near or below this limit. See, Akhter, M. S., *Effect of acetamide on the critical micelle concentration of aqueous solutions of some surfactants.* Colloids and Surfaces A:

Physicochemical and Engineering Aspects, 1997. 121(2-3): p. 103-109, and Verma, N. K., S. K. Khanna, and B. Kapila, *Comprehensive Chemistry XII*. 2015, each of which is incorporated by reference in its entirety. Thirdly, as a result of using concentration near the CMC, the emulsions made by Sumner are unstable, multimodal, and high dipersity, with the resultant solution showing sedimentation due to coalescence within few hours of the formation process.

Vapor condensation on pure oils (without any emulsifier) has been studied by numerous authors before. A common method for vapor condensation on an oil involves cooling down the oil below the dew point of the vapor. A vapor of a primary liquid may have affinity with the secondary liquid due to which the molecules of the primary liquid may be absorbed within the secondary liquid through permeation. See, Barrer, R. M. and E. K. Rideal, *Permeation, diffusion and solution of gases in organic polymers*. Transactions of the Faraday Society, 1939. 35: p. 628-643; Wijmans, J. G. and R. W. Baker, *The solution-diffusion model: A review*. Journal of Membrane Science, 1995. 107(1-2): p. 1-21; and Merkel, T. C., et al., *Gas sorption, diffusion, and permeation in poly(dimethylsiloxane)*. Journal of Polymer Science Part B: Polymer Physics, 2000. 38(3): p. 415-434, each of which is incorporated by reference in its entirety. For most of the gases/vapors, the dissolution in a liquid is an exothermic process, because of which the solubility limit of vapor in liquids increases when the temperature is decreased. As a result, when a secondary liquid with dissolved vapor (of the primary liquid) is cooled it becomes under-saturated. See, Moore, J., C. Stanitski, and P. Jurs, *Principles of chemistry: the molecular science*. 2009: Cengage Learning; Griswold, J. and J. E. Kasch, *Hydrocarbon-Water Solubilities at Elevated Temperatures and Pressures*. Industrial & Engineering Chemistry, 1942. 34(7): p. 804-806; and Poddar, T. K. and K. K. Sirkar, *Henry's law constant for selected volatile organic compounds in high-boiling oils*. Journal of Chemical and Engineering Data, 1996. 41(6): p. 1329-1332, each of which is incorporated by reference in its entirety. Consequently, the molecules of the primary liquid cannot supersaturate within the secondary liquid and droplet nucleation of the primary liquid within the secondary liquid cannot occur. Because of this, nucleation is most favored at the oil-air interface. See, Sushant Anand, Konrad Rykaczewski, Srinivas Bengaluru Subramanyam, Daniel Beysens and Kripa K. Varanasi, *How droplets nucleate and grow on liquids and liquid impregnated surfaces*, Soft Matter, 2015, 11, 69, which is incorporated by reference in its entirety.

Figure 13:
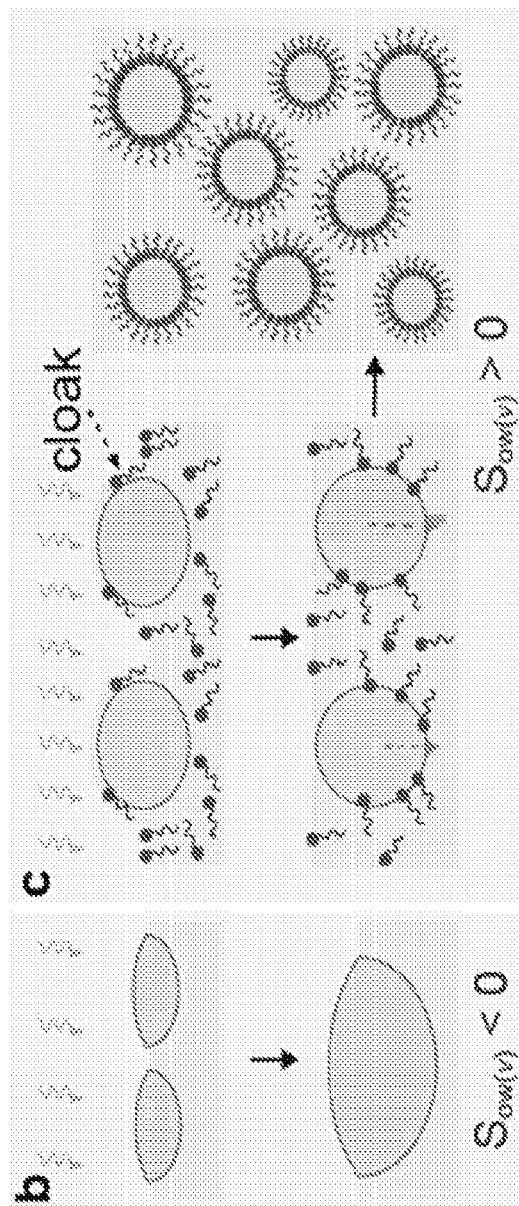
FIG. 13 shows a schematic for condensation on non-cloaking oils, and on oil-emulsifier systems that have tendency to spread (i.e. cloak) on droplets nucleated at the oil-air interface.

Once the droplets have nucleated on pure oil, the evolution of droplet size is largely dependent upon the interfacial interactions between the primary liquid and the secondary liquid. To explain this, we consider an example of nucleation of water droplets on oils. Two liquids in contact with each other may have a tendency to spread on each other. The spreading tendency can be found by evaluating the spreading coefficient of one liquid with respect to the other liquid. In particular, water droplet growth is suppressed through coverage of droplet by a liquid with positive spreading coefficient with respect to water, i.e. $S_{od(a)} = \gamma_{da} - \gamma_{oa} - \gamma_{do} > 0$ ($\gamma_{da}$, $\gamma_{oa}$ and $\gamma_{do}$ is the surface tension of condensate (water here), surface tension of the oil, and the interfacial tension between oil-condensate respectively). See, Sushant Anand, Adam T. Paxson, Rajeev Dhiman, J. David Smith, and Kripa K. Varanasi, *Enhanced Condensation on Lubricant-Impregnated Nanotextured Surfaces*. ACS Nano, 2012. 6(11): p. 10122-10129, which is incorporated by reference in its entirety. This mechanism is referred from now on as "cloaking" and this mechanism also leads to submergence of droplets within the liquid to produce dispersed water droplets within the liquids (FIG. 13). See, Sushant Anand, Konrad Rykaczewski, Srinivas Bengaluru Subramanyam, Daniel Beysens and Kripa K. Varanasi, *How droplets nucleate and grow on liquids and liquid impregnated surfaces*, Soft Matter, 2015, 11, 69, which is incorporated by reference in its entirety. On the other hand, condensation on non-cloaking liquids (i.e. $S_{od(a)} = \gamma_{da} - \gamma_{oa} - \gamma_{do} > 0$) does not lead to submergence of condensed droplets. See, A. Scheludko, V. Chakarov, and B. Toshev, *Water condensation on hexadecane and linear tension*. Journal of Colloid and Interface Science, 1981. 82(1): p. 83-92; CM Knobler and D. Beysens, *Growth of breath figures on fluid surfaces*. Europhysics Letters, 1988. 6(8): p. 707-712; A. Steyer, P. Guenoun, D. Beysens, and C. M. Knobler, *Two-dimensional ordering during droplet growth on a liquid surface*. Physical Review B, 1990. 42(1): p. 1086-1089; A. D. Alexandrov, B. V. Toshev, and A. D. Scheludko, *Nucleation from supersaturated water vapour on immiscible liquid substrates: Effect of the macroscopic geometry of the three-phase system on the critical supersaturation and the line tension*. Colloids and Surfaces A: Physicochemical and Engineering Aspects, 1993. 79(1): p. 43-50, and Sushant Anand, Adam T. Paxson, Rajeev Dhiman, J. David Smith, and Kripa K. Varanasi, *Enhanced Condensation on Lubricant-Impregnated Nanotextured Surfaces*. ACS Nano, 2012. 6(11): p. 10122-10129 each of which is incorporated by reference in its entirety. However, on cloaking or non-cloaking liquids, the droplet coalescence is rapid due to absence of any stabilizing mechanism leading to formation of large droplets. On the other hand, here the idea is based on condensation of vapor phase of a primary liquid on a secondary liquid (the continuous medium) in the presence of stabilizing additives such as surfactants, nanoparticles coated with surfactants or other materials, that adsorb at the interface of the droplet-oil and stabilize the dispersed phases against immediate coalescence of the droplets for long time usage.

The method disclosed herein relies on vapor condensation of the primary liquid (or dispersed phase, d) wherein the concentration of the stabilizing agent in the secondary liquid (i.e. continuous phase, o) is larger than a minimum critical value (see FIG. 1). The stabilizing agents may be emulsifiers such as surfactants or nanoparticles that have the chemistry which provides hindrance against coalescence of droplet phases. In case where the stabilizing agents are surfactants (single of combination of many different surfactants), the minimum critical value is defined by the CMC of the solution, wherein CMC is the value beyond which the surfactant molecules form micelles within the secondary liquid. The disclosed method herein is not limited in injection of a vapor phase directly within a continuous medium. In an embodiment of this disclosure, the droplets can nucleate at the oil-air interface, the oil-emulsifier solution may then spread on the nucleated droplets (because the spreading coefficient of the oil-emulsifier solution may be positive i.e. $S_{od(a)}=\gamma_{da}-\gamma_{oa}-\gamma_{do}>0$). The spreading of oil-emulsifier solution on nucleated droplets cause them to submerge within the oil-emulsifier solution due to capillary forces leading to formation of emulsions even when the oil (continuous medium) is not agitated or the vapor phase has negligible velocity. In another embodiment of this disclosure, the droplets can nucleate at the oil-air interface and form a film at the oil-air interface if the spreading coefficient of the droplet with respect to the oil-air interface is positive (i.e. $S_{od(a)}=\gamma_{da}-\gamma_{oa}-\gamma_{do}>0$), the film may then be broken into droplets due to instabilities induced by the action of vapor carrying sufficient pressure/velocity, and the droplets may then get submerged within the oil. In addition, precise control over the size and number density of the droplets within a continuous medium is possible. Through this technique, smaller (nanoscale) emulsions (<1 µm diameter) can also be made. A wider scope of materials that may be used using this method. The formation of both oil-in-water and water-in-oil emulsions are demonstrated. In one embodiment shown in the results, non-ionic surfactants were used in the case of water-in-oil emulsions, and both ionic and non-ionic surfactants were used in the case of oil-in-water emulsions. The disclosed method herein makes it possible to use a wider range of oils and surfactants to form safer and more suitable emulsions for various products.

The method disclosed herein relies on vapor condensation of the dispersed medium (d) wherein the concentration of the stabilizing agent in the continuous medium (o) is larger than a minimum critical value. In case where the stabilizing agents are surfactants (single of combination of many different surfactants), the minimum critical value is defined by the CMC of the solution, wherein CMC is the value beyond which the surfactant molecules adsorb to form micelles. Also, the disclosed method herein is not limited in injection of a vapor phase directly within a continuous medium. In certain embodiments, the droplets can nucleate at the oil-air interface, get cloaked and submerge, and form emulsions even when the oil (continuous medium) is not agitated or the vapor phase has negligible velocity. In addition, precise control over the size and number density of the droplets within a continuous medium is possible. Through this technique, smaller (nanoscale) emulsions (<1 µm diameter) can be made. Sumner's method only reports on the formation of micron-sized emulsions (1-10 µm). A wider scope of materials that may be used using this method. The formation of both oil-in-water and water-in-oil emulsions are demonstrated. In one embodiment shown in the results, non-ionic surfactants were used in the case of water-in-oil emulsions, and both ionic and non-ionic surfactants were used in the case of oil-in-water emulsions. In other embodiments, other type of surfactants can be used such as anionic, zwitterionic, polymeric, liquid-crystals, biosurfactants, etc. The disclosed method herein makes it possible to use a wider range of oils and surfactants to form safer and more suitable emulsions for various products. In another embodiment, the emulsifier may be added in-situ during the vapor condensation process. Possible mechanisms through which the emulsifier may be added can include, but are not limited to: spraying of emulsifier on the secondary liquid, the spray being formed by aerosolization techniques, or injected through nozzles within or outside the secondary liquid.

Disclose herein is a method of making emulsions using the droplets formed and dispersed in a continuous phase (oil) by the nucleation mechanism, and the coalescence of such droplets delayed through use of a stabilizing agent present in the continuous phase by condensing vapor of the droplet phase in the oil in presence of a stabilizing mechanism such as surfactants or nanoparticles that have the chemistry which provides hindrance against coalescence of droplet phases (see FIG. 1). A subcooled liquid comprising of oil (o) and emulsifier (e) with temperature below the dew point of vapor temperature in air is exposed to humid air (v). At (a) a nuclei is formed on the surface. At (b), a thin film of the oil-emulsifier system spread on the droplet. At (c), the formation of the thin film around the droplet leads to submergence of the droplet. At (d), new nuclei may form on top of the oil-emulsifier system, and steps (a)-(c) are repeated. Eventually in step (e) many droplets immersed within the liquid may be obtained. An advantage of this method is that droplets of dispersed phase can be generated from monodisperse sizes to polydisperse sizes and the size range of droplets can be controlled from nano-sizes to micron sizes depending upon the exposure time during condensation.

With the approach disclosed herein, oil in water type or water in oil type emulsions can be prepared. The prerequisite of formation involves production of vapor of one species, and subsequent condensation on other liquid. Since there are multiple ways of generating vapor, the system can be adapted to condense oils on water also. Oil in oil type emulsions can also be prepared with this method, if the two oils are immiscible or partly miscible with each other. Monodisperse or polydisperse droplet sizes in oils can be formed, and the size of the droplets can be controlled and nanoemulsions and microemulsions can be formed. With this approach, any emulsifier suitable for the system can be used. For example, surfactants or nanoparticles with suitable surface chemistry can be included to provide hindrance to coalescence. This method can be combined with the previously existing technologies and used in conjunction with them to generate emulsions. This approach allows generating wide variety of emulsions. The critical requirement is generation of vapor of one phase (droplet phase) and condensation on the continuous phase, and the two phases should be immiscible with each other. This method does not require any mechanical stirring and emulsions can be formed even in small confinements or small quantities of the secondary liquid. Multiple emulsions can also be formed by this method, such as double emulsions (oil in water droplets, and the encapsulated droplet in an oil).

Condensation of a vapor occurs requires a condensing vapor and a medium that can provide with necessary energy to absorb the latent heat of vapor to liquid transformation. Examples of such systems include mediums that are sub-cooled below the temperature of the vapor species, and depend upon the thermodynamic environment i.e. whether the medium is liquid or air. The vapor phase of a condensing liquid can be generated by several means. Examples of vapor generation techniques include, but are not limited to: evaporation of a liquid, boiling of a liquid, aerosolizing nanometric droplets and vaporizing them by applying heat, or decreasing the pressure of the system containing the condensing liquid to vaporize the liquid.

To make nanoscale water-in-oil emulsions using condensation, an oil reservoir was placed in a temperature-controlled, humid environment. When the temperature of the oil is lowered, small water droplets condense on the surface of the oil once the dew point is surpassed. The oil (which may contain surfactants) covers the surface of the water drops once they are condensed. Broadly speaking, this technique may be used to create a wide range of water-in-oil or oil-in-water emulsions. The precise size, chemical composition, and density of emulsions may be controlled through varying the experimental parameters, such as surfactant concentration, time of condensation, humidity, and temperature. Specifically, the formation of water-in-oil emulsions was demonstrated using dodecane (oil), Span 80 (oil surfactant), and water vapor. The size and polydispersity of these emulsions have been characterized and the size of the emulsions generally increases as the concentration of oil surfactant decreases, or as the time of condensation increases. Emulsions with different oils/surfactants, such as kerosene/Span 80, as well as dodecane/Span 85 have been demonstrated. The formation of oil-in-water emulsions by condensing cyclohexane vapor on water containing sodium dodecyl sulfate and Tween 80 (water surfactants) has been demonstrated.

This method is capable of working with variety of liquids. Some examples of liquids that could be used for preparing emulsions include: water; hydrocarbon oils such as linear or branched alkanes (including but not limited to butane, pentane, hexane, heptane, octane, nonane, decane, undecane, dodecane, tridecane, tetradecane, pentadecane, hexadecane); cyclic alkanes (including but not limited to cyclobutane, cyclopentane, cyclohexane, cycloheptane); linear or branched alkenes (including but not limited to squalene); cyclic and/or aromatic compounds (including but not limited to benzene, toluene); hydrocarbon oils with hydroxyl groups and/or esters and/or ethers (including but not limited to food derivatives, such as castor oil, olive oil, sunflower seed oil); alcohols such as linear or branched alcohols (including but not limited to methanol, ethanol, propanol, butanol, pentanol, hexanol, heptanol, octanol, nonanol, decanol, undecanol); cyclic or aromatic compounds with hydroxyl groups; silicone oils of different viscosities and with different termination groups; mineral oils; fluorinated oils (including but not limited to perfluorinated carbon-based oils such as the FC series oils e.g. FC-40, FC-70 & fluorinated oils with ethers e.g. Krytox, Cytop).

In this method, the choice of dispersed phase (d) can depend upon the ability to create a vapor phase of the liquid to be dispersed. Any liquid (amongst examples of liquids discussed above) can be dispersed within a continuous phase as long as its vapor can be generated and subsequently be condensed. Examples of vaporization techniques may include and are not limited to: heating, or pressure reduction. In this method, any liquid (amongst examples of liquids discussed above) can be used as the continuous phase as long as it exists in the liquid state under the thermodynamic conditions where the vapor to liquid phase change of the dispersed phase may occur.

The primary purpose of the stabilizing agent is to delay the coalescence of the droplets by encapsulating the dispersed droplets. The stabilizing agent can be natural or synthetic. In one embodiment, the stabilizing agent can be a surfactant having at-least two different parts—each having a separate affinity for the dispersed phase and the continuous phase while being antagonistic towards the other phase. For example, a surfactant can have a hydrophilic part that has affinity for water phase, and is antagonistic towards oil phase; and a hydrophobic part that has affinity for oil phase, and is antagonistic towards water phase. The stabilizing agent can be non-ionic surfactant including Spans (e.g. Span 20, Span 40, Span 60, Span 65, Span 80, Span 83, Span 85), Tweens (e.g. Tween 20, Tween 21, Tween 40, Tween 60, Tween 61, Tween 65, Tween 80, Tween 85), glycerin, ethylene glycol, glyceryl laurate, dodecyldimethylamine oxide, polyethoxylated tallow amine (POEA), glucoside alkyl ethers; anionic surfactants including sodium tetradecyl sulfate, sodium dodecyl sulfate (SDS), sodium decyl sulfate, sodium octyl sulfate, sodium oleate, dioctyl sulfosuccinate sodium salt (AOT); cationic surfactants including hexadecyltrimethylammonium bromide, cetyltrimethylammonium bromide; zwitterionic surfactants; polymeric and/or block co-polymer surfactants including poloxamers, polyoxyethylene glycol alkyl ethers (e.g. Brij 58), polyoxyethylene glycol alkylphenol ethers (e.g. Nonoxynol-9), polyoxyethylene glycol octylphenol ethers (e.g. Triton X-100), polyoxypropylene glycol alkyl ethers, polyoxyethylene glycol alkylphenol ethers (e.g. nonoxynol-9), polyethylene glycol (PEG); ionic liquid surfactants; stimuli-responsive surfactants; gemini surfactants; Janus particles (comprising of regions of hydrophilic/hydrophobic wettabilities); or solid particles including polymer compounds (e.g. latex), inorganic compounds (e.g. silica, titania). See, Kronberg, B., K. Holmberg, and B. Lindman, *Surface Chemistry of Surfactants and Polymers.* 2014: John Wiley & Sons, Ltd. 1-47, which is incorporated by reference in its entirety.

The choice of surfactant/emulsifier to prepare a desired type of emulsion (example: water-in-oil or oil-in-water or oil-in-oil) is contingent upon whether the emulsifier adsorbs at the interface of the dispersed and continuous phase. In general, surfactants with low hydrophilic lipophilic balance (HLB) values are miscible with lipophilic/non-polar liquids such as oils, and surfactants with high HLB values are miscible with hydrophilic/polar liquids such as water. Surfactants with low HLB values are generally used to create water-in-oil emulsions, whereas surfactants with high HLB values are generally used to form oil-in-water emulsions. Some combinations for making water in oil emulsions that have been prepared include (and are not limited to): Dodecane/water/Span 80, Dodecane/water/Span 85, Kerosene/water/Span 80, Squalene/water/Span 80, Castor oil/water/Span 80. Some combinations for making oil in water emulsions that have been prepared include (and are not limited to): Cyclohexane/water/Tween 80+SDS.

This method is fundamental in nature and hence could be used in a wide variety of applications. In pharmaceutical/drug industries: oil in water or water in oil emulsions are widely used in form of ointments, pastes, films, or medicine also. With this technique, emulsions with very small sized dispersed phases can be obtained, and these can be directly used in above-mentioned applications. Micro-emulsions are also used as vaccines to kill microbes, and such formulations can be prepared by this technique. In food industry, emulsions are used in deserts, beverages, etc., such emulsions can be easily prepared with this technique. In aircraft and utilities, many types of automobile oils are based on oil in oil or oil in water or water in oil type emulsions. Such emulsions can be prepared with this technique. In cosmetics, emulsions such as hand-creams, lotions, hair-sprays can be easily prepared with this technique. In agrochemicals, emulsions used as mechanism for delivering insecticides, pesticides, fungicides etc. can be easily prepared with this technique. In heat transfer oils, water in oil, or oil in oil type emulsions used for enhancing heat transfer in many devices, can be prepared with this technique.

Making Emulsions by Surface Condensation on an Oil

Figure 2A:
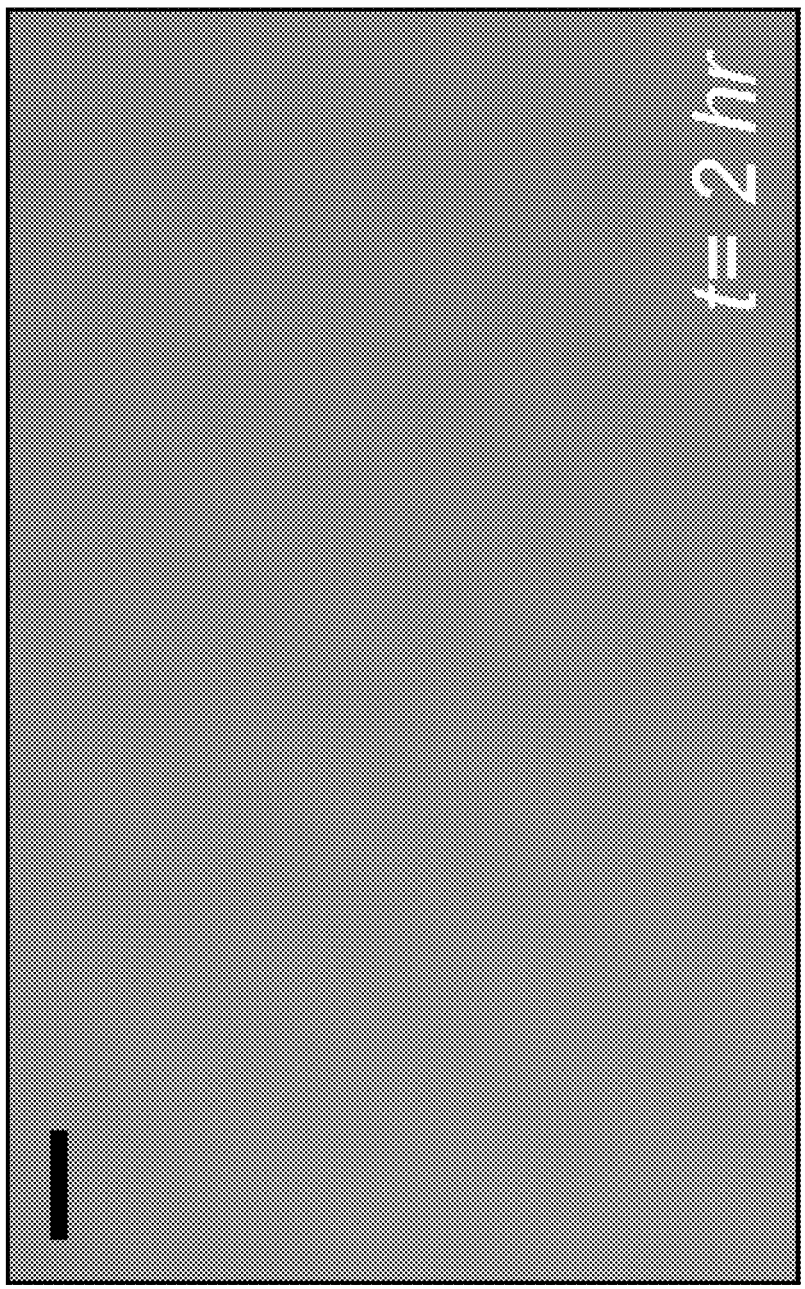
FIGS. 2A-B show an example of condensation on a subcooled liquid (silicone oil here) exposed to humid air.
Figure 2B:
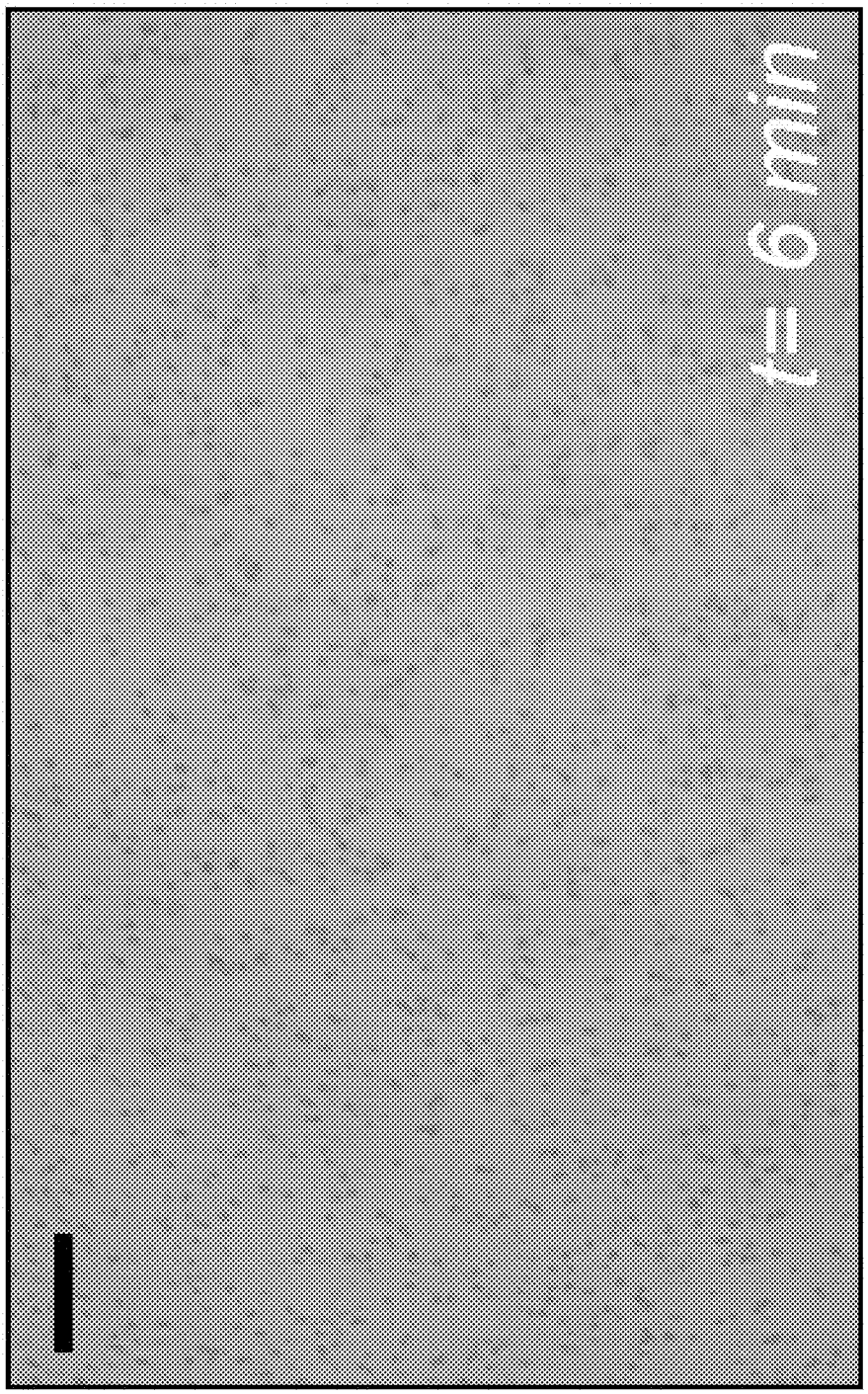

Condensation of a vapor occurs on a surface when there is a temperature difference between the condensing vapor and the surface, and the surface temperature is below the dew-point of the vapor species. As an example, FIG. 2A shows that droplet formation does not occur in the oil when the oil is subcooled but not below the dew point of the vapor of the primary liquid (in this case water). However, as the temperature of the liquid is cooled below the dew point (FIG. 2B), condensation occurs on the surface of the liquid leading to formation of large number of droplets (appearing as black dots).

Condensation on oils can lead to formation of dispersed droplets within the liquid. However, the droplets can coalesce rapidly in absence of a surfactant. Addition of a stabilizing agent like emulsifier can on the other hand lead to formation of a stable emulsion. As an example, FIGS. 3A-E show the formation of a stable emulsion of water in oil in presence of a surfactant, and show the difference compared to condensation on a bulk liquid in absence of a surfactant. Condensation on silicone oil with surfactant leads to stable emulsion formation that remained translucent for several days. The droplet phase size is expected to be sub-micron in size. Left side photos show condensation of water vapor on subcooled bulk silicone oil liquid without Emulsifier. Right side photos show condensation of water vapor on subcooled bulk Silicone Oil liquid with Emulsifier (a surfactant, in this case sodium dodecyl sulfate).

Figure 3A:
FIGS. 3A-E show image sequences of condensation of water vapor on subcooled bulk silicone oil with and without the presence of a surfactant.
Figure 3B:
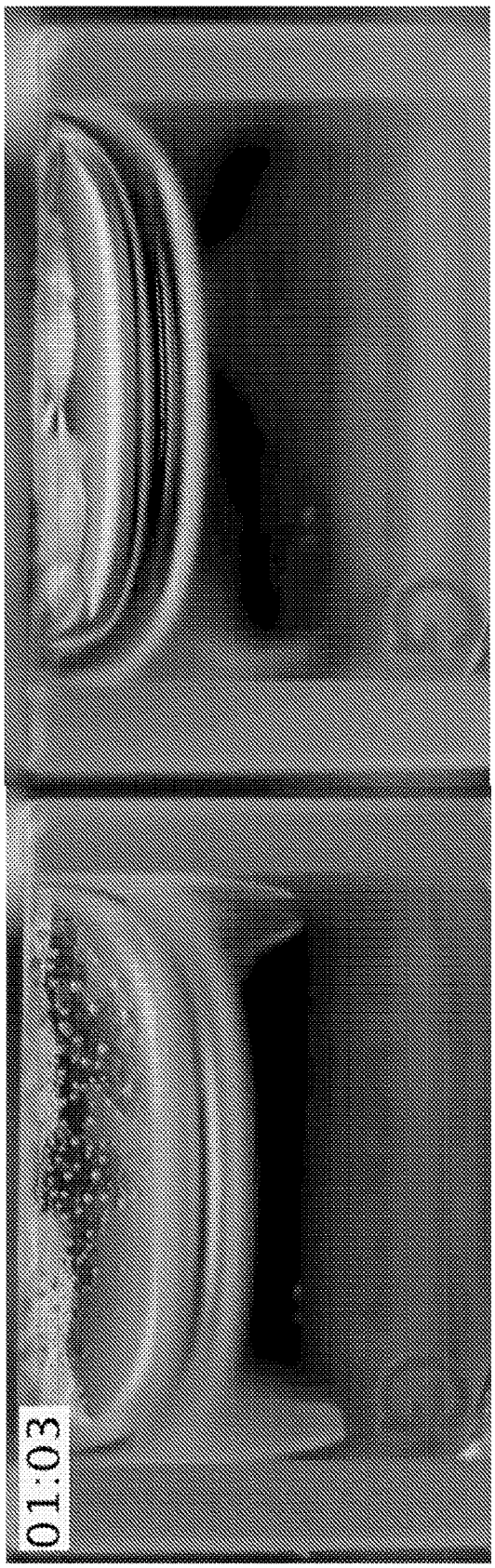
Figure 3C:
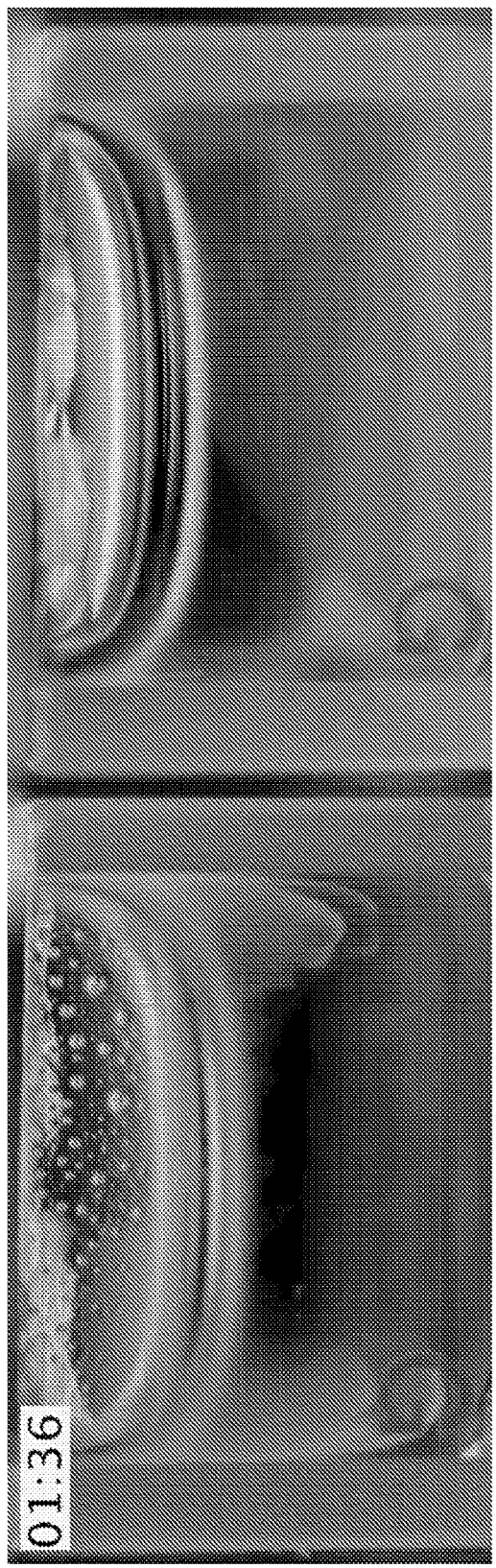
Figure 3D:
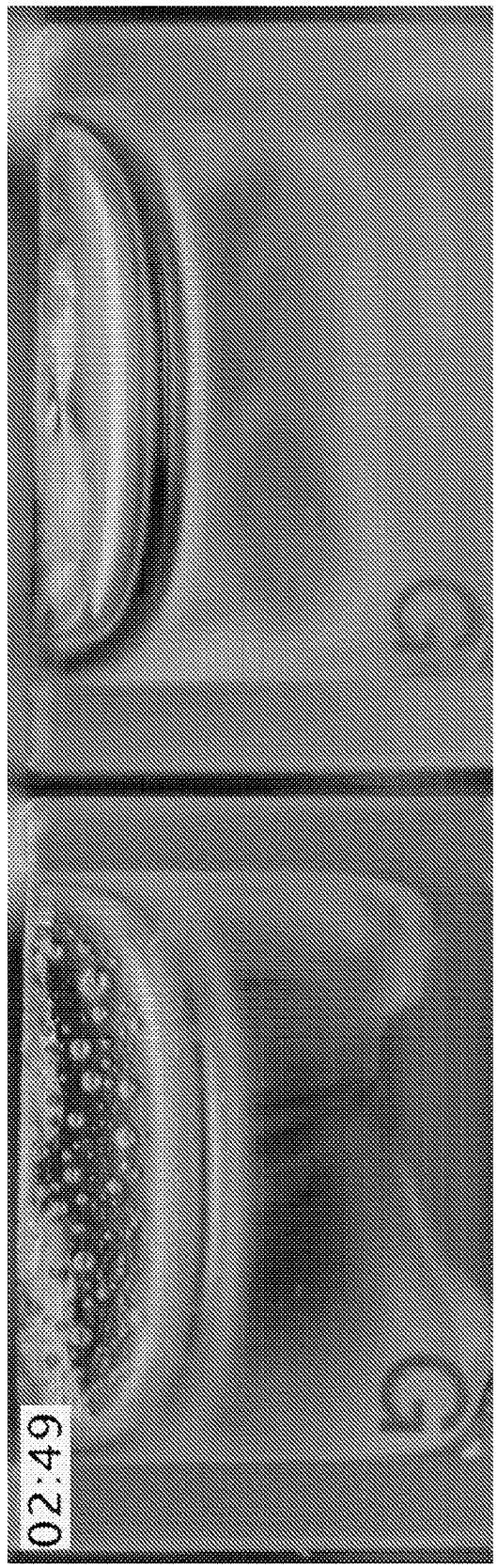
Figure 3E:
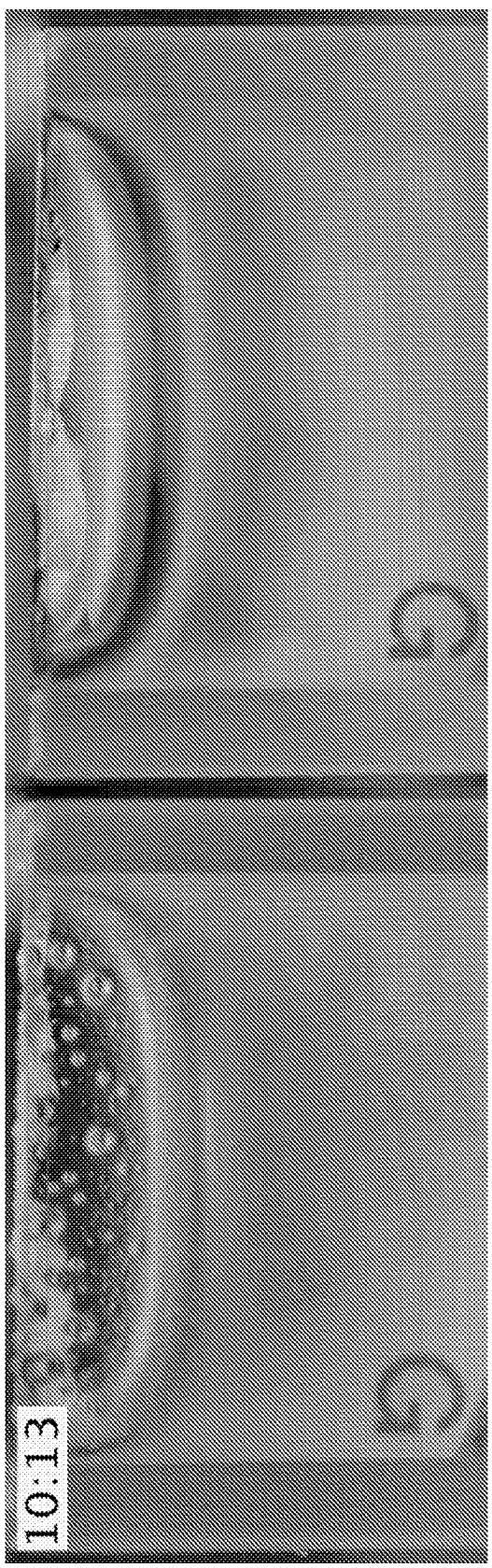

In FIG. 3A (time 00:00), the silicone oil (viscosity 10 cSt) was subcooled to temperature below the dew point and experiments were performed on condensation on the bulk liquid with and without the surfactant. The size of the cuvette is 10 mm (the distance between the glass walls observable in these images). In FIG. 3B (time 01:03), on plain bulk Silicone oil surface, large droplets formed near the wall within seconds of formation. Whereas no visible large sized droplets were observed in the cuvette filled with silicone oil and the surfactant. A mild haziness instead develops in the liquid. In FIG. 3C (time 01:36), on plain bulk Silicone oil surface, the droplets grow in size. Haziness or milkiness spreads within the liquid, but large droplets are clearly visible within the liquid. On the other hand, in case of silicone oil and surfactant solution, only increased milkiness of the solution is observed with no detectable droplet of any size. The formation of this milkiness shows that the droplets are sub-microscopic in size. In FIG. 3E (time 10:13), on plain bulk Silicone oil surface, large droplets can be found increasing in size and coalescing at different locations (at the surface or within the liquid). In case of oil and surfactant mixture, the entire solution is translucent due to formation of large number of droplets within the solution. The size of the droplets remains sub-microscopic and invisible to the naked eye.

Figure 7A:
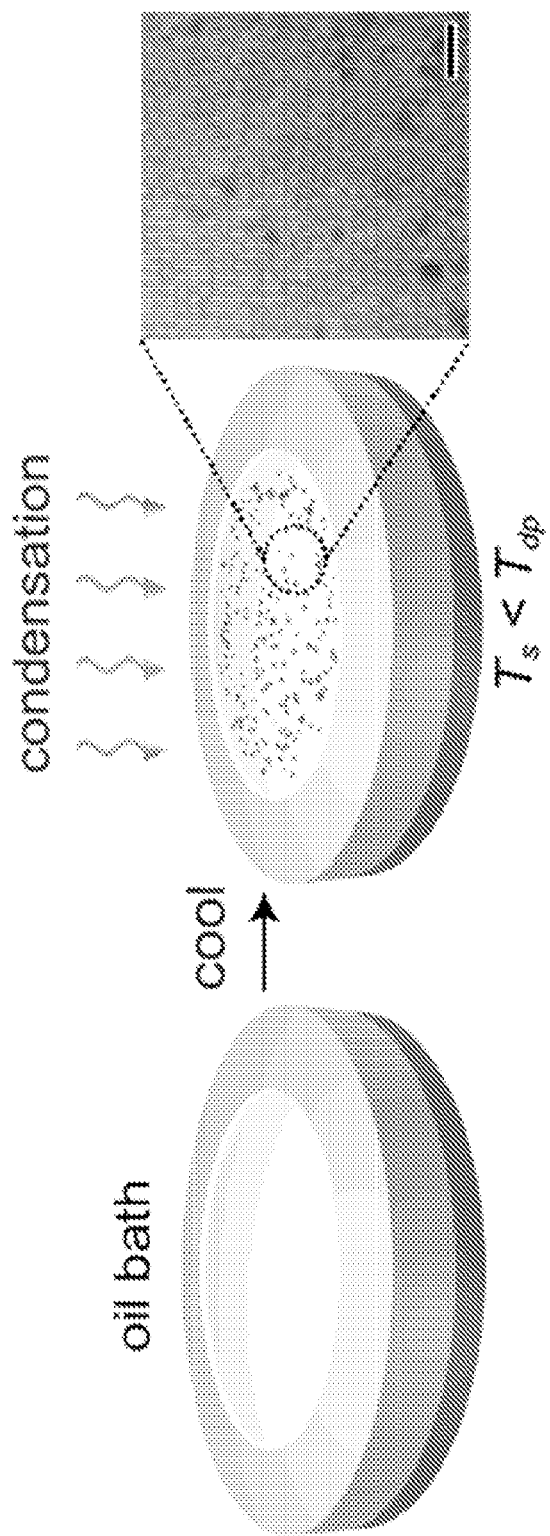
FIG. 7A shows a setup for making nanoemulsions via condensation.
Figure 7B:
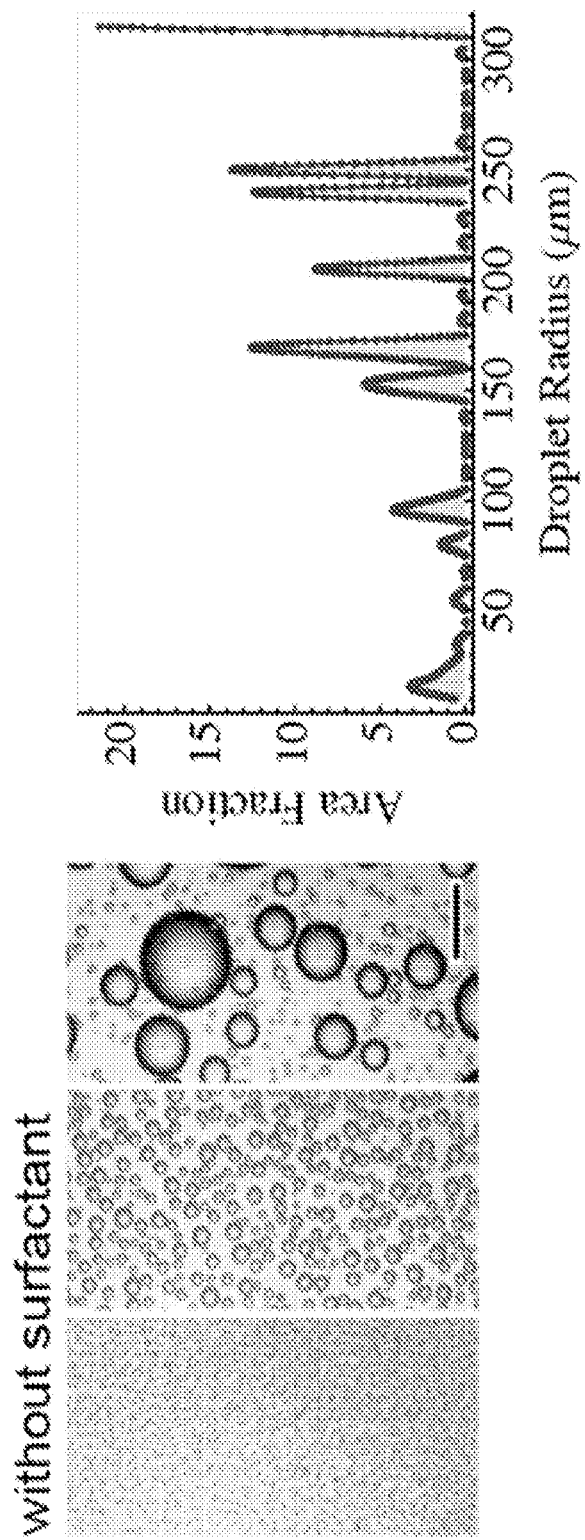
FIGS. 7B and 7C show condensation on oil without and with surfactant, respectively.
Figure 7C:
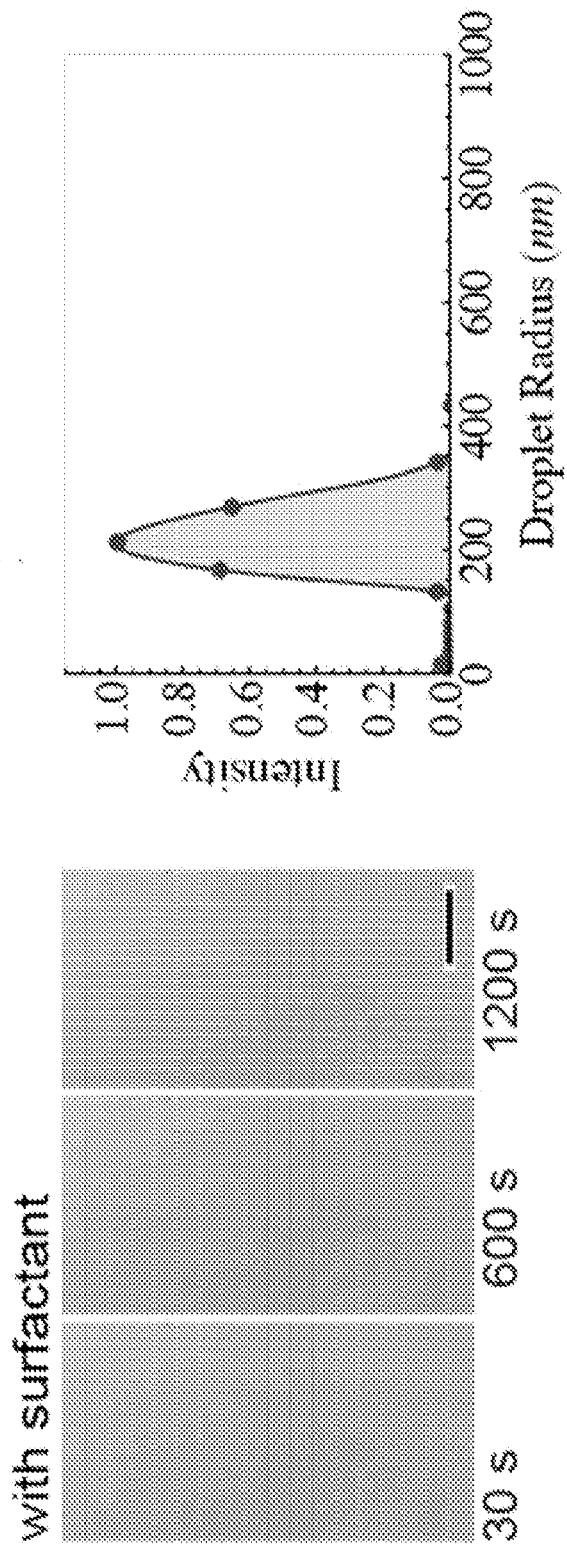

In another example, water vapor was condensed on oil in a container by subcooling the oil below the dew point of the water vapor (FIG. 7A). Pure dodecane was used as oil since dodecane has a negative spreading coefficient with respect to water, and does not spread on water. Condensation of water vapor on pure dodecane led to formation of micron sized droplets with large polydispersity (FIG. 7B). Thereafter, pure dodecane was replaced by dodecane with a surfactant (Span 85) wherein the concentration of Span 85 was 100 times the CMC of Span85 in dodecane. Water vapor was subsequently condensed on the dodecane-Span85 solution, and this led to formation of droplets that were too small to be measured optically (FIG. 7C). Using dynamic light scattering, the droplet sizes were evaluated in nano sizes (FIG. 7C) with very low polydispersity (<20%) confirming the formation of nanoemulsions.

The formation of the dispersed phase (droplets) in the continuous phase (oil) can be achieved through multiple ways using condensation. In certain embodiments, the oil can be subcooled below dew point of the vapor of the condensing liquid (henceforth referred as vapor only), and the vapor of the immiscible liquid condenses at the oil-air interface. For such liquids, an emulsion will be formed if the oil or oil-emulsifier system spread on the droplets. The key parameter dictating this state is given by spreading coefficient of oil-emulsifier solution on the droplet. In certain embodiments, the oil may be at a temperature $T_{oil}$, and the vapor maybe superheated. Upon contact of the superheated vapor and the oil, the vapor may condense on the surface of the oil and emulsion may form if the oil or oil-emulsifier system spread on the droplets. In certain embodiments, the oil may also flow across a surface with a velocity $V_{oil}$, and the vapor may itself flow with a velocity $V_{vapor}$. In certain embodiments, the oil may also be agitated such as by using techniques that are currently employed for producing of emulsions by shear-stress across the oil (mechanical stirring, ultrasonic stirring, etc.) during the process of vapour condensation on the oil. In certain embodiments, vapour may be condensed on a mixture of two oils where one oil is miscible with the condensing liquid, and the other is immiscible liquid. In certain embodiments, the droplets may themselves have tendency to spread at the oil-emulsifier interface, but the thin films may be broken spontaneously or by action of the vapour velocity leading to formation of droplets which then may get submerged within the oil by the action of the vapour velocity.

Emulsion by Direct Vapor Injection in an Oil

Figure 4A:
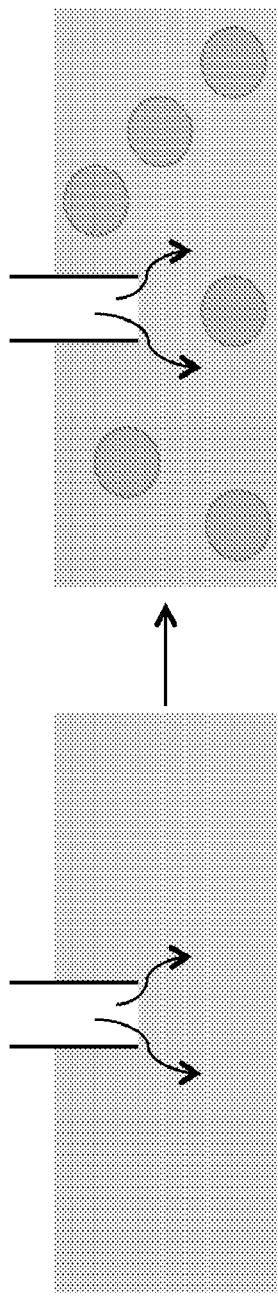
FIGS. 4A-B show a schematic of two different embodiments involving vapor injection in a subcooled oil leading to formation of emulsions.
Figure 4B:
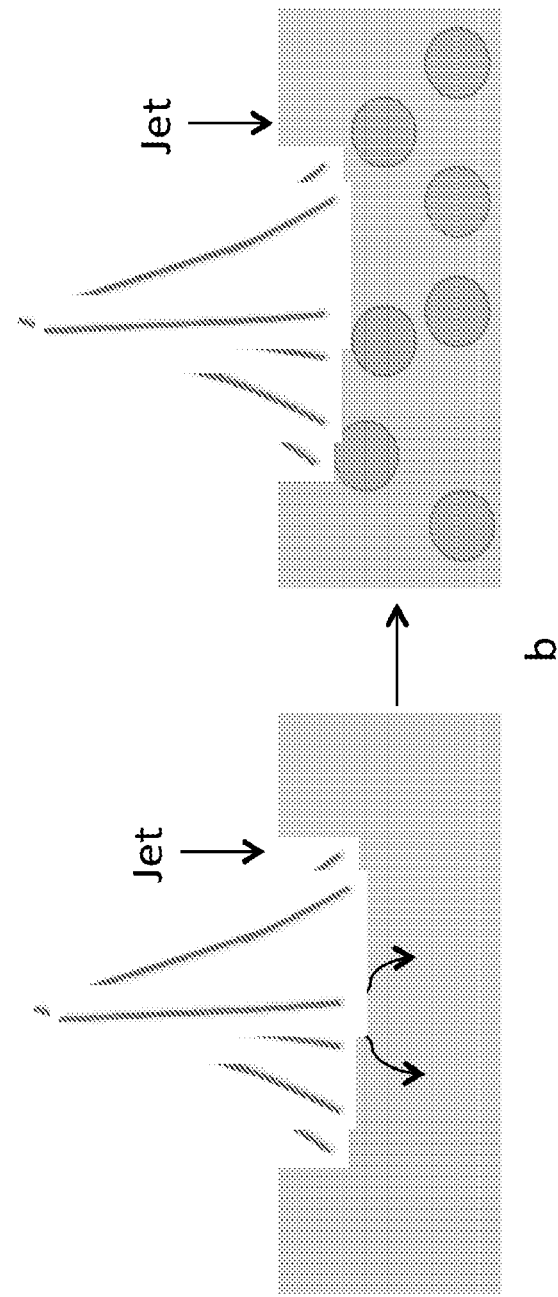

In certain embodiments, the vapor can be directly injected into the oil-emulsifier system and condensing the vapor within such system. Here, a key requirement is that the oil-emulsifier system must be able to provide the necessary cooling of the injected vapor. The vapor injection in an oil-emulsifier system may be achieved through multiple methods. Few examples where this system may be used are envisioned as: use of a tube immersed directly within the oil-emulsifier system (FIGS. 4A-B), use of jet impingement of vapor on a subcooled oil-emulsifier system. FIG. 4A shows vapor injection through an immersed pipe. FIG. 4B shows vapor injection through jet of vapor impinging on the oil. Here the droplet sizes have been shown much larger for ease of understanding.

In certain embodiments, the oil may also flow across a surface with a velocity $V_{oil}$, and the vapor may itself flow with a velocity $V_{vapor}$. In certain embodiments, the oil may also be agitated such as by using techniques that are currently employed for producing of emulsions by shear-stress across the oil (mechanical stirring, ultrasonic stirring, etc.) during the process of vapour condensation on the oil.

Emulsion by Injection of Vapor in a Microchannel/Membrane

Figure 5:
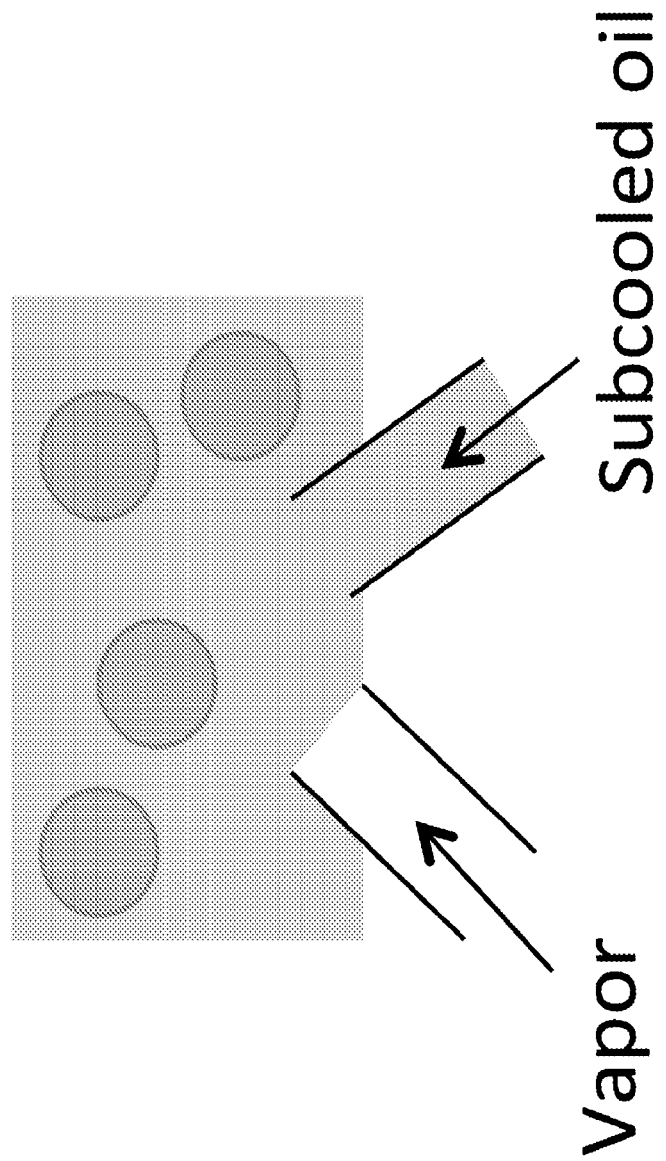
FIG. 5 shows a schematic of the embodiment involving vapor injection in a subcooled oil leading through channels, and where both the vapor and the oil have a flow rate.

In some embodiments of the invention, the vapor source can be injected through microchannels or membranes or porous walls within an oil-emulsifier system. FIG. 5 shows a schematic of the embodiment involving vapor injection in a subcooled oil leading through channels. The size of the channels can range from nanopores to millimetric sized pores. The size of channels, droplets is exaggerated for ease of understanding.

Double Emulsion by Condensation of Two Vapors on an Oil

Figure 6A:
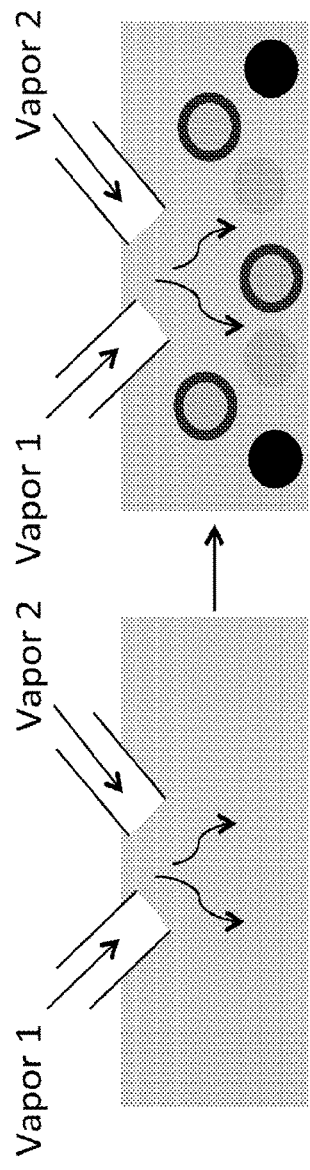
FIGS. 6A-B shows a schematic of two embodiments involving formation of double emulsions.
Figure 6B:
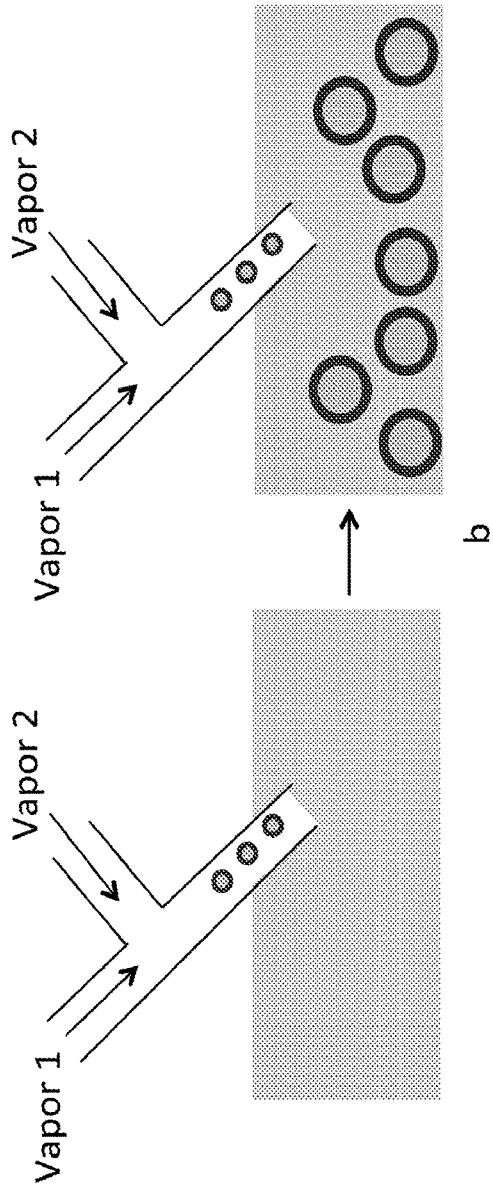

In some embodiments of the invention, two or more vapor sources may be condensed simultaneously on the oil-emulsifier system. FIGS. 6A-B show a schematic of the embodiment involving formation of double emulsions. The blue color denotes condensing liquid of vapor species 1, the black color denotes the condensing liquid of vapor species 2, and the oil/oil-emulsifier system is shown in orange. The size of channels, droplets is exaggerated for ease of understanding. The condensation of two or more sources may be done in a parallel manner (FIG. 6A) or serially (FIG. 6B). The serial manner of vapor injection may lead to more homogeneous formation of double emulsions as compared to parallel method of injecting vapor.

Controlling the Size and Number Density of Dispersed Droplets in an Oil

In other methods, the micro/nano-emulsion formation involves breaking of a larger sized droplet to smaller droplets. On the other hand, condensation of a vapor by default leads to formation of nuclei that are in nanometeric size ranges. As compared to the other techniques that rely on emulsifiers to help in decreasing the shear forces to break the droplets, this technique does not rely on surfactants for this explicit purpose. Rather, emulsifiers (e.g. surfactants) are used for stabilizing the dispersed phase in continuous phase for an extended period of time.

In our method, the size, density and polydispersity of emulsions may be controlled through varying the experimental parameters, such as emulsifier concentration, exposure time of condensing vapor to the oil, humidity, and temperature. As an example, in FIG. 8 we show that water vapor was condensed in identical thermodynamic conditions (dew point, humidity, subcooling) and identical periods of time (~2 minutes) on dodecane with different concentrations of the surfactant. When the concentration of surfactant was <cmc, highly polydisperse emulsion was obtained that was unstable. When the concentration of surfactant was ~cmc value, the mean droplet size decreased to forming microscale emulsions. When the concentration of the surfactant was made 10 times the cmc, the dispersed size of droplets further decreased in size and the polydispersity was reduced as well. When the concentration of the surfactant in the dodecane was made 100 times the cmc, the resultant droplet size after condensation decreased to nanoscales and very monodisperse nanoemulsions were obtained (FIG. 9).

In another example, water vapour was condensed on dodecane with surfactant under identical conditions and identical surfactant concentration but for different time periods of condensation. The concentration of the surfactant was ~100 times the cmc value. Emulsions were obtained by condensing for different periods of time. The results (FIG. 11) indicate that by increasing the time periods of condensation, the size of the emulsion droplets increased from nanoemulsions to microemulsions along with increase in the polydispersity.

Examples

FIG. 7A shows the setup for making nanoemulsions via condensation. Oil was placed in a chamber with top surface of the oil exposed to air. The chamber consisted of a copper plate (chamber bottom) attached to a Teflon ring (chamber sides). The oil is about 5 mm thick from the bottom. The oil can include surfactants. Oil was cooled in the chamber by cooling the copper bottom to 2° C. The bulk oil cools. Relative humidity of air above oil chamber was kept constant around 75-80%. Exceeding the dew point (by lowering the temperature and maintaining high humidity) leads to condensation on the oil surface.

If certain conditions are met, condensed water droplets stabilize in the nanometric range. For example, surfactant concentration must be sufficiently high to stabilize emulsions; otherwise they coalesce and grow indefinitely. FIG. 7B shows the emulsion size distribution without surfactants and FIG. 7C shows the emulsion size distribution with surfactants.

Figure 8:
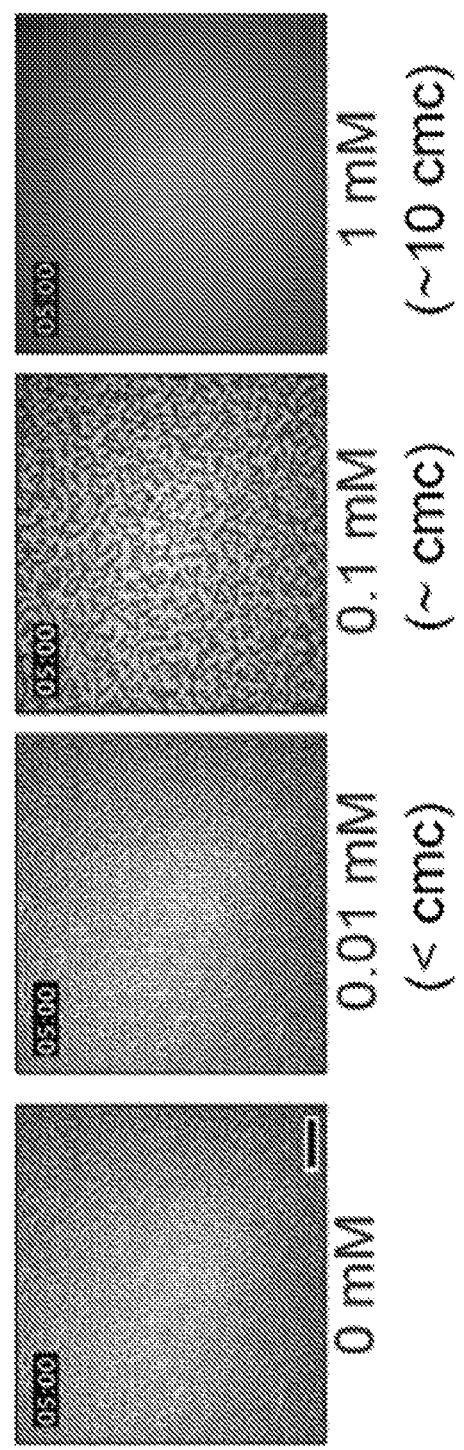
FIG. 8 shows a series of photos depicting effect of increasing surfactant concentration in the oil on the droplet size. The thermodynamic conditions and the exposure time of vapor condensation on the oil were identical.
Figure 9:
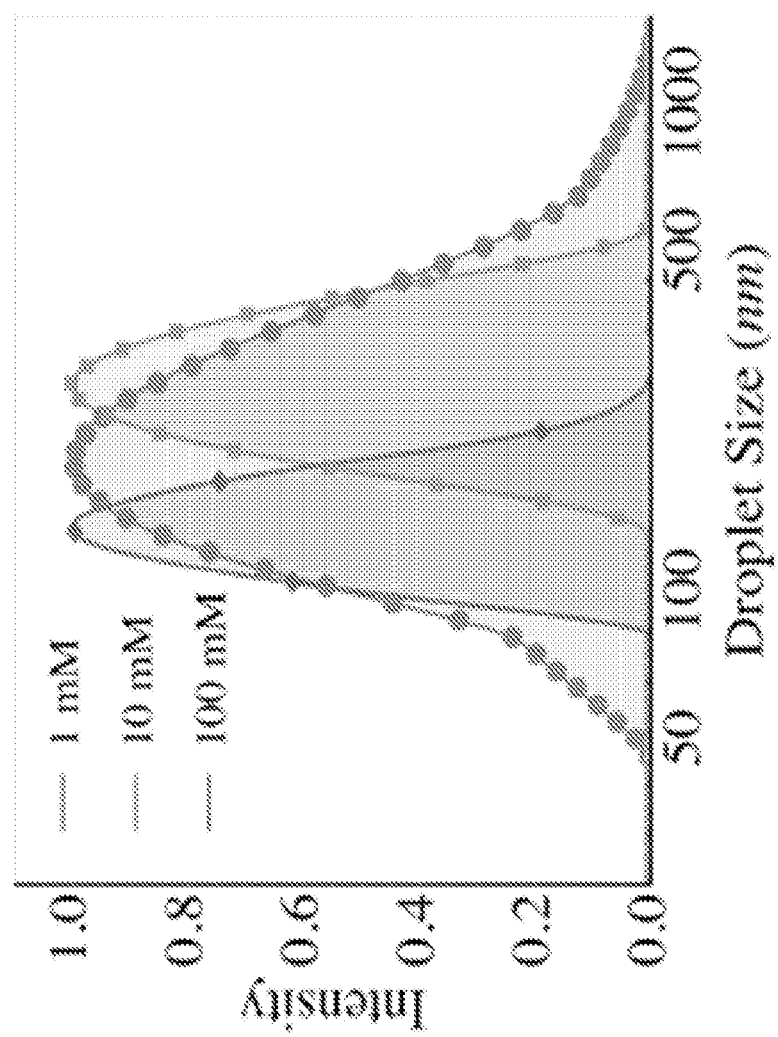
FIG. 9 shows a graph depicting DLS (Dynamic Light Scattering) results that indicates the size range of droplets formed in oil with different surfactant concentrations. The thermodynamic conditions and the exposure time of vapor condensation on the oil were identical.

FIG. 8 shows that increasing oil surfactant concentration decreases the emulsion size. For surfactant concentrations≤0.1 mM, the resulting emulsions are greater than 1 μm in size. For surfactant concentrations≥1 mM surfactant, the emulsions are nanoscale (below 1 μm in size).

FIG. 9 shows the effect of oil surfactant concentration on nanoemulsion size. As the surfactant concentration increases, the resulting emulsion radius shifts in size and polydispersity. At the lowest concentration of surfactant, the radius peak is quite broad (signalling higher polydispersity). As the surfactant concentration is increased, the peak narrows (indicating lower polydispersity) and the emulsion size generally becomes smaller. All surfactant concentrations in this range result in nanoscale emulsions.

Figure 10:
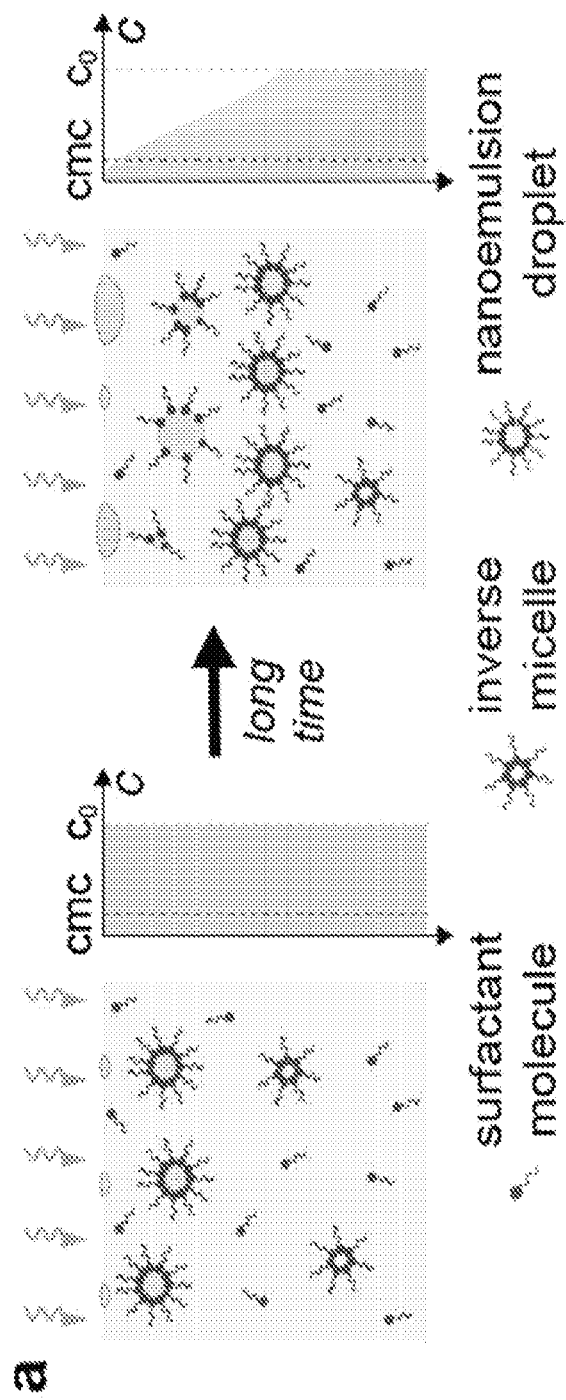
FIG. 10 depicts a possible mechanism of surfactant adsorption on nucleating droplets during the condensation process. It is shown that the formation of droplets in an oil with a fixed concentration of surfactant may result in decrease in concentration of free surfactant molecules as vapor condensation time increases.
Figure 11:
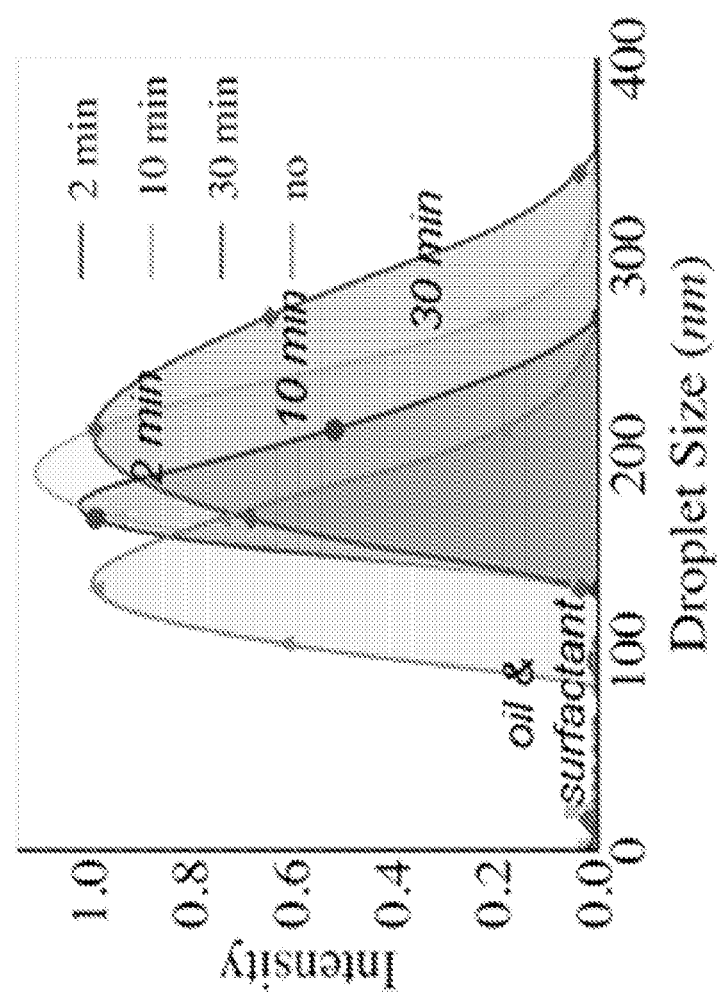
FIG. 11 shows a graph depicting DLS (Dynamic Light Scattering) results that indicate the effect of condensation time on nanoemulsion size and polydispersity. The thermodynamic conditions and the concentration of surfactant within the oil were identical.

FIG. 10 shows a schematic diagram that the size and polydispersity of the emulsion generally decrease as the time of condensation decreases. FIG. 11 shows the effect of condensation time on nanoemulsion size and polydispersity. The emulsion remains in the nanoscale region even after 30 minutes of condensation.

Figure 12:
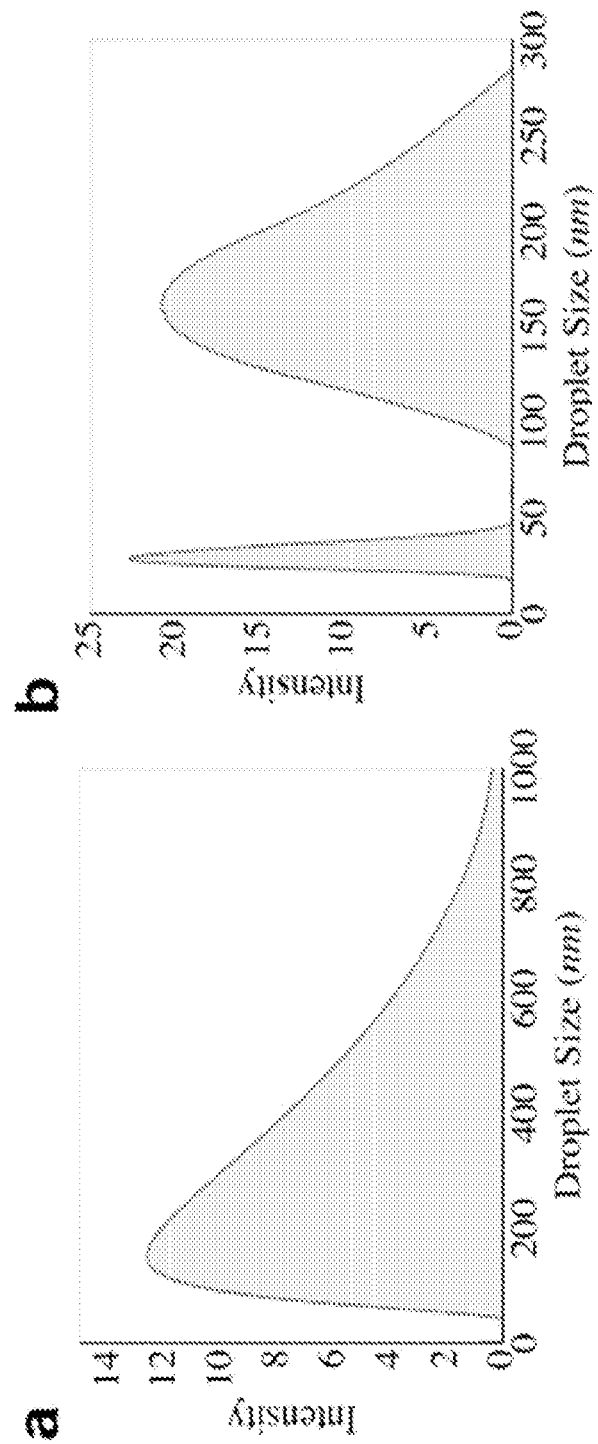
FIG. 12 shows graphs depicting DLS results for cyclohexane-in-water emulsions (left) and water-in-kerosene emulsions (right).

FIG. 12 shows DLS results for cyclohexane-in-water emulsions (left) and water-in-kerosene emulsions (right). Both sets of emulsions are nanoscale. Time of condensation for both experiments: 2 minutes. Water phase used to make the cyclohexane emulsion contained sodium dodecyl sulfate and Tween 80. Kerosene contained 100 mM Span 80.

Other embodiments are within the scope of the following claims.

What is claimed is:

1. A method of making an emulsion comprising:
vaporizing a primary liquid;
selecting a secondary liquid and an emulsifier to permit formation of an emulsion, wherein the primary liquid and the secondary liquid are immiscible or partly miscible and the emulsifier concentration is larger than its minimum critical concentration; and
forming a mixture of the primary liquid, the secondary liquid and the emulsifier under thermodynamic conditions that are below the dew point of the primary liquid, and
subcooling the second liquid below the dew point of the vapor of the secondary liquid.

2. The method of making an emulsion of claim 1, wherein the emulsion is monomodal in size.

3. The method of making an emulsion of claim 2, wherein the monomodal emulsion is nanoscale.

4. The method of making an emulsion of claim 3, wherein the monomodal emulsion is directly formed without further processing to reduce emulsion size.

5. The method of making an emulsion of claim 1, wherein a temperature of the secondary liquid is below the dew point of the primary liquid.

6. The method of making an emulsion of claim 1, wherein the primary liquid is water and the secondary liquid is oil.

7. The method of making an emulsion of claim 1, wherein the primary liquid is oil and the secondary liquid is water.

8. The method of making an emulsion of claim 1, wherein the primary liquid is a first oil and the secondary liquid is a second oil.

9. The method of making an emulsion of claim 1, further comprising superheating the vaporized liquid before condensing.

10. The method of making an emulsion of claim 1, wherein the vaporizing the primary liquid includes evaporating the primary liquid by heating, boiling the primary liquid, aerosolizing the primary liquid and heating the aerosol droplets of the primary liquid, or decreasing pressure surrounding the primary liquid.

11. The method of making an emulsion of claim 1, wherein the emulsifier is a surfactant.

12. The method of making an emulsion of claim 1, wherein the emulsifier is nanoparticles.

13. The method of making an emulsion of claim 1, wherein the method further comprising flowing the secondary liquid and the vaporized primary liquid.

14. The method of making an emulsion of claim 1, wherein the method further comprising agitating the secondary liquid while condensing the vaporized primary liquid.

15. The method of making an emulsion of claim 1, wherein the condensing the primary liquid on the secondary liquid comprising injecting the vaporized primary liquid into the secondary liquid.

16. The method of making an emulsion of claim 1, wherein the condensing the primary liquid on the secondary liquid comprising using jet impingement of the vaporized liquid.

17. The method of making an emulsion of claim 1, wherein the condensing the primary liquid on the secondary liquid comprising injecting through microchannels or membranes or porous walls within a secondary liquid-emulsifier mixture.

18. The method of making an emulsion of claim 1, wherein the emulsifier is a surfactant and the minimum critical concentration is a critical micelle concentration of the surfactant.

19. The method of making an emulsion of claim 1, wherein the emulsifier is a nanoparticle and the minimum critical concentration is an equilibrium concentration at which the nanoparticles have maximum adsorption at the interface.

20. The method of making an emulsion of claim 1, wherein the emulsifier is added in-situ during a vapor condensation process.

21. The method of making an emulsion of claim 1, wherein vaporization includes evaporation of a liquid, boiling of a liquid, aerosolizing nanometric droplets and vaporizing them by applying heat, or decreasing the pressure of the system containing the condensing liquid to vaporize a liquid.

22. A method of making an emulsion comprising:
vaporizing a primary liquid;
selecting a secondary liquid and an emulsifier to permit formation of an emulsion, wherein the primary liquid and the secondary liquid are immiscible or partly miscible and the emulsifier concentration is larger than its minimum critical concentration; and
forming a mixture of the primary liquid, the secondary liquid and the emulsifier under thermodynamic conditions that are below the dew point of the primary liquid, further comprising vaporizing the emulsion and thereafter condensing the emulsion on a tertiary liquid.

23. A method of making an emulsion comprising:
vaporizing a primary liquid;
selecting a secondary liquid, a tertiary liquid and an emulsifier to permit formation of an emulsion, wherein the primary liquid and the secondary liquid are immiscible;
subcooling the primary liquid below the dew point of the vapor of the secondary liquid and
condensing the primary liquid on a mixture of the secondary liquid and the tertiary liquid, wherein the secondary liquid is miscible with the tertiary liquid and the tertiary liquid is immiscible with the primary liquid.

24. The method of making emulsions of claim 23, wherein the primary liquid is water.

25. The method of making emulsions of claim 23, wherein the secondary liquid is a first oil, and the tertiary liquid is a second oil.

26. The method of making an emulsion of claim 23, wherein the emulsion is monomodal in size.

27. The method of making an emulsion of claim 26, wherein the monomodal emulsion is nanoscale.

28. The method of making an emulsion of claim 27, wherein the monomodal emulsion is directly formed without further processing to reduce emulsion size.

29. The method of making an emulsion of claim 23, wherein the emulsion further comprises an emulsifier.

* * * * *